(12) United States Patent
Armstrong et al.

(10) Patent No.: US 7,220,777 B2
(45) Date of Patent: May 22, 2007

(54) LACTAM DERIVATIVES AS ANTAGONISTS FOR HUMAN 11CBY RECEPTORS

(75) Inventors: Sula Anne Armstrong, Cambridge (GB); Dieter Wolfgang Hamprecht, Verona (IT); Martin Jones, Harlow (GB); David Richard Witty, Harlow (GB); Kamal A Al-Barazanji, Durham, NC (US); Mohammad Tadayyon, Hertford (GB)

(73) Assignee: SmithKline Beecham P.L.C., Brentford, Middlesex (GB)

( * ) Notice: Subject to any disclaimer, the term of this patent is extended or adjusted under 35 U.S.C. 154(b) by 0 days.

(21) Appl. No.: 10/492,062

(22) PCT Filed: Oct. 15, 2002

(86) PCT No.: PCT/US02/32740

§ 371 (c)(1),
(2), (4) Date: Apr. 8, 2004

(87) PCT Pub. No.: WO03/033480

PCT Pub. Date: Apr. 24, 2003

(65) Prior Publication Data

US 2005/0059651 A1    Mar. 17, 2005

(30) Foreign Application Priority Data

Oct. 15, 2001    (GB) ................... 0124627.1

(51) Int. Cl.
| | | |
|---|---|---|
| C07D 403/10 | (2006.01) | |
| A61K 31/4035 | (2006.01) | |
| A61P 3/04 | (2006.01) | |
| A61P 3/10 | (2006.01) | |
| A61P 25/18 | (2006.01) | |
| A61P 25/22 | (2006.01) | |
| A61P 25/24 | (2006.01) | |

(52) U.S. Cl. .................... 514/422; 514/423; 548/566; 548/567

(58) Field of Classification Search ............... 548/566, 548/567; 514/422, 423
See application file for complete search history.

(56) References Cited

FOREIGN PATENT DOCUMENTS

| WO | WO 97/41097 | 11/1997 |
|---|---|---|
| WO | WO 01/21577 | 3/2001 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48; 3-26, 2001.*
Mashiko et al., Endocrinology 146(7): 3080-3086, 2005.*
Saxena S et al., *Anti-Inflammatory Quinazolinoes*, Indian Journal of Pharmaceutical Sciences 53(2): 48-52 (Mar. 1991).
Database Caplus Online, Chemical Abstrats Service, Coloumbus Ohio, US, Database accession No. 1991:122049 XP002233183 abstract & PL 137 227 B (Uniwersytel Lodzki, Lodz (Polska) Mar. 31, 1987 table.

* cited by examiner

Primary Examiner—Venkataraman Balasubramanian
(74) Attorney, Agent, or Firm—Bonnie L. Deppenbrock

(57) ABSTRACT

The invention provides compounds of formula (I)

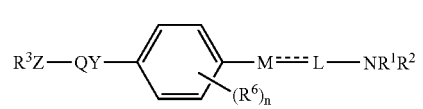

a salt, or solvate thereof.

14 Claims, No Drawings

LACTAM DERIVATIVES AS ANTAGONISTS FOR HUMAN 11CBY RECEPTORS

This application is filed pursuant to 35 U.S.C. § 371 as a United States National Phase Application of International Application No. PCT/US02/32740 filed Oct. 15, 2002, which claims priority from GB 0124627.1 filed Oct. 15, 2001.

This invention relates to novel lactam derivatives which are antagonists at the human 11CBy receptors, to processes for their preparation, to pharmaceutical compositions containing them and to their uses in therapy.

WO01/21577 (Takeda) relates to a compound of the formula

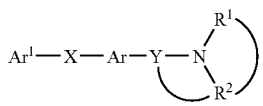

wherein $Ar^1$ is a cyclic group which may have substituents, X is a spacer having a main chain of 1 to 6 atoms, Y is a bond or a spacer having a main chain of 1 to 6 atoms, Ar is a monocyclic aromatic ring which may be condensed with a 4 to 8 membered non-aromatic ring, and may have further substituents; $R^1$ and $R^2$ are independently hydrogen or a hydrocarbon group which may have substituents; $R^1$ and $R^2$ together with the adjacent nitrogen atom may form a nitrogen containing hereto ring which may have substituents; $R^2$ may form a spiro ring together with Ar or $R^2$ together with the adjacent nitrogen atom may for a nitrogen containing hereto ring which may have substituents, or a salt thereof; and which compounds are antagonists of a melanin concentrating hormone. Such compounds are suggested as being useful for preventing or treating obesity.

We have now found a novel group of compounds that exhibit a useful profile of activity as antagonists of the human 11CBy receptor (also referred to as MCHR1) disclosed in Nature 400, 261–265 (1999).

SUMMARY OF THE INVENTION

The invention thus provides compounds of formula (I)

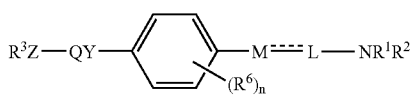

(I)

a salt or solvate thereof, wherein

M is a group selected from the group consisting of O, S, C=O, NH and $CH_2$;

L is a 2 or 3 membered alkylene chain;

wherein together M-L may be optionally substituted by at least one moiety selected from the group consisting of methyl, ethyl, hydroxy and $C_{1-3}$ alkoxy;

(i) $R^1$ and $R^2$ are each independently selected from the group consisting of hydrogen, $C_{1-6}$ straight or branched alkyl which may be optionally substituted by phenyl, and $C_{3-6}$ cycloalkyl optionally substituted by one or more $C_{1-6}$ alkyl groups;

or (ii) $R^1$ and $R^2$ together with the nitrogen atom to which they bonded form a 4–8 member heterocyclic ring or a 7–10 membered heterocyclic ring containing 1, 2, or 3 heteroatoms selected from N, O and S, wherein said 4 to 8 membered heterocyclic ring and said 7 to 10 membered bicyclic heterocyclic ring are optionally substituted with a substituent selected from the group consisting of phenyl and from one to four $C_{1-3}$ alkyl;

each $R^6$ is the same or different and is independently selected from the group consisting of hydroxy, $C_{1-2}$alkyl, $C_{1-3}$alkoxy, halo, $C_{2-3}$alkenyl, benzyl, and $—C(R^a)NOR^b$, wherein $R^a$ and $R^b$ are each independently selected from the group consisting of hydrogen, methyl, methoxymethyl, methoxymethoxyl, and methoxyethoxyl; and n is 1, 2, 3, or 4;

QY is a bicyclic fused heterocyclic ring wherein Q and Y are each one ring of said bicyclic fused heterocyclic group, wherein said Y ring contains from 1 to 3 nitrogens and is bound to the phenyl ring of formula (I) via a nitrogen atom, and said Q ring is a 5 or 6 membered aryl or heterocyclic ring having a group $ZR^3$; Z is bound to the Q ring;

Z is selected from the group consisting of a direct bond, NH, $NCH_3$, O, S or $CH_2$; and $R^3$ is a group selected from the group consisting of aryl, alk-2-en-1-yl, cycloalkyl and cycloalk-2-en-1-yl and wherein said aryl, alk-2-en-1-yl, cycloalkyl, and cycloalk-2-en-1-yl are optionally substituted from 1 to 3 times with a subsittuent selected from the group consisting of $C_{1-3}$ alkyl, halo, amino, alkylamino, dialkylamino, hydroxy, $C_{1-3}$ alkoxy, cyano, trifluoromethyl, and methylthio groups.

The invention also includes embodiments to (i) a pharmaceutical formulation comprising a compound of formula (I), (ii) the use of a compound of formula (I) or a pharmaceutical formulation comprising the formula (I) in therapy, and (iii) processes for the preparation of a compound of formula (I).

DETAILED DESCRIPTION OF THE INVENTION

In the present invention, unless otherwise stated, references to salts, include both physiologically acceptable salts and non-physiologically acceptable salts of compounds of formula (I). The compounds of formula (I) and salts thereof may form solvents (e.g. hydrates) and the invention includes all such solvates.

As used herein, "a compound of the invention or a compound" of formula (I) means a compound of formula (I) or a pharmaceutically acceptable salt, or solvate thereof.

As used herein, the term "optionally" means that the subsequently described event(s) may or may not occur, and includes both event(s) that occur and events that do not occur.

The term "alkyl" as a group or part of a group (e.g., alkoxy, alkylamino, etc.) refers to a straight or branched alkyl group. Said alkyl contains from 1 to 6 carbon atoms unless otherwise specified. Examples of such $C_{1-6}$ alkyl groups include methyl, ethyl, propyl, isopropyl, butyl, isobutyl, t-butyl, pentyl, neopentyl or hexyl.

The term "alk-2-en-1-yl" refers to a straight or branched $C_{3-6}$ alk-2-en-1-yl group.

The term "cycloalkyl" refers to non-aromatic monocyclic carbocyclic rings having 3 to 7 carbon atoms which may be substituted by a moiety selected from the group consisting of hydroxy, $C_{1-3}$ alkoxy, and halo.

The term "halo" or "halogen" refers to the elements fluorine, chlorine, bromine, and iodine, unless otherwise specified.

The term "cycloalk-2-en-1-yl" refers to a $C_{5-7}$ cycloalk-2-en-1-yl group.

The term "aryl" preferably refers to phenyl, but also includes fused aryl rings such as naphthyl.

The terms "heterocycle" and "heterocyclic" refer to a ring system composed of C and at least one other atom selected from the group consisting of N, O, and S. Heterocycles may or may not be heteroaromatic as defined below. In other words, heteroaromatics are heterocycles, but all heterocycles are not heteroaromatic.

The term "heteroaryl" and "heteroaromatic" refer to a monocyclic or bicylic aromatic ring system composed of C and at least one other atom selected from the group consisting of N, O, and S.

The terms "members" (and variants thereof, e.g., "membered") in the context of heterocyclic and heteroaryl groups refers to the total atoms, carbon and heteroatoms (N, O, and/or S) which form the ring. Thus, an example of a 6-membered heterocyclic ring is piperidine and an example of a 6-membered heteroaryl ring is pyridine.

In formula (I), M is selected from the group consisting of O, S, C=O, NH, and $CH_2$. Preferably M is O or $CH_2$. Most preferably, M is O.

L of formula (I) is 2 to 3 membered alkylene chain (that is, $(CH_2)_2$ or $(CH_2)_3$). Preferably, L is $(CH_2)_2$. When the group L is linked to the phenyl ring of formula (I) via a $R^6$ substituent, said $R^6$ is located in the ortho position to the group M. Examples of the resultant bicyclic structure include 1,4-benzodioxan; benzopyran; 1,2-dihydrobezopyran; 1,2,3,4-tetrahydronaphthalene; and 1,2-dihydronaphthalene.

In formula (I), in (i) $R^1$ and $R^2$ are each independently selected from the group consisting of hydrogen, $C_{1-6}$ straight or branched alkyl which may be optionally substituted by phenyl, and $C_{3-6}$ cycloalkyl optionally substituted by one to four $C_{1-6}$ alkyl groups. When $R^1$ and $R^2$ independently represent $C_{1-6}$ alkyl, then preferred examples of such $R^1$ and $R^2$ groups include methyl and isopropyl.

Alternatively, in (ii) $R^1$ and $R^2$ together with the nitrogen atom to which they are bonded form a 4–8 membered heterocyclic ring or a 7–10 membered bicyclic heterocyclic ring (containing 1, 2, or 3 heteroatoms selected from N, O and S), wherein said 4 to 8 membered heterocyclic ring and said 7 to 10 membered bicyclic heterocyclic ring are optionally substituted with a substituent selected from the group consisting of phenyl and from one to four $C_{1-3}$ alkyl.

When $R_1$ and $R_2$ together with the nitrogen atom to which they are bonded or attached form a 4–8 membered heterocyclic ring, examples of such rings include azetendinyl, pyrrolidinyl or piperidinyl, which rings may be substituted by 1–4 methyl groups or a phenyl group (e.g. pyrrolidinyl, 2-methylpyrrolidinyl, 2,5-dimethyl-pyrrolidinyl, piperidyl, 2-methylpiperidinyl, 2,6-dimethylpiperidinyl, 2,2,6,6, tetramethylpiperidinyl or 4-phenylpiperidinyl).

When $R^1$ and $R^2$ together with the nitrogen atom form a bridged heterocyclic ring, examples of such groups include 7-aza-bicyclo [2.2.1]hept-7-yl or 2-aza-bicyclic [2.2.2] oct-8-yl.

Preferably, the group $NR^1R^2$ is a tertiary amino group; more preferably a 4–8 membered heterocyclic ring which may be substituted by 1–4 methyl groups; or an optionally substituted 5- or 6-membered heterocycle. In the most preferred embodiment of the invention, $NR^1R^2$ is a pyrrolidinyl group.

Each $R^6$ is the same or different and is independently selected from the group consisting of hydrogen, $C_{1-2}$alkyl $C_{1-3}$alkoxy, halo, $C_{2-3}$alkenyl, benzyl, and —$C(R^a)NOR^b$, wherein $R^a$ and $R^b$ are each independently selected from the group consisting of hydrogen, methyl, methoxymethyl, methoxymethoxy, and methoxyethoxy. Typically, $R^6$ is a substituent of the phenyl ring of formula (I) that is preferably located in the ortho position relative to the M substituent. Preferred examples of $R^6$ include hydroxy, methoxy, methoxymethoxy, methoxyethoxy, and methoxymethyl. Most preferably, $R^6$ is methoxy. In the formula, n is 1, 2, 3, or 4.

QY is a bicyclic fused heterocyclic ring wherein Q and Y are each one ring of said bicyclic fused heterocyclic group, wherein said Y ring contains from 1 to 3 nitrogens and is bound to the phenyl ring of formula (I) through a nitrogen, and said Q ring is a 5 or 6 membered aryl or heteroaryl having a group $ZR^3$ bound to the Q ring.

The fused bicyclic heterocyclic group QY is preferably a 5,5; 5,6; 6,5; or 6,6 bicyclic heterocyclic system.

In QY group, Q is conveniently an aromatic ring such as benzene, thiophene, furan or pyridine. Y, in QY, is linked via a nitrogen atom therein to the rest of the molecule in formula (I) and optionally contains a further 1 or 2 nitrogen atoms. Preferably, the ring-also contains a carbonyl group adjacent to the linking nitrogen atom.

When Y is a 5-membered ring, it contains either two carbonyl groups or a carbonyl and a methylene group, in addition to the nitrogen atom. When Y is a 5-membered ring, then preferably Q is a benzene ring, and more preferably QY is an isoindole-1,3-dione.

When Y is a 6-membered ring, it preferably contains a carbonyl group and either two additional nitrogen atoms or a single additional nitrogen and a moiety selected from the group consisting of carbonyl, thiocarbonyl, and methylidene. Said moiety can be optionally substituted by a member selected from the group consisting of methyl, methoxy, methylthio, and $S(O)CH_3$. When Y is a 6-membered ring, Q is preferably a benzene or thiophene ring.

Examples of suitable QY groups include isoindole-1,3-dione, 2,3-dihydro-isoindole-1-one, 3-H-benzo[d](1,2,3)triazin-4-one, 3-H-quinazolin-4-one, 1-H-quinazoline-2,4-dione, 3-H-thieno[2,3-d]-1-triazine-4-one, 3-H-thieno[2,3d]pyrimidin-4-one, 3-H-thieno[3,2-d]pyrimidin-4-one, 2-thioxo-2,3-dihydro-1-H-thieno[3,2-d]pyrimidine-4-one, 2-methylsulphanyl-3H-thieno[3,2-d]pyrimidin-4-one.

Z is selected from the group consisting of a direct bond, NH, $OCH_3$, O, S, and $CH_2$. Preferably, examples of suitable groups Z include a bond, oxygen, sulphur, $CH_2$ or NH. Most preferably, the group Z is a bond or an oxygen atom.

$R^3$ is a group selected from the group consisting of aryl, alk-2-en-1-yl, cycloalkyl and cycloalk-2-en-1-yl and wherein said aryl, alk-2-en-1-yl, cycloalkyl, and cycloalk-2-en-1-yl are optionally substituted from 1 to 3 times with a substituent selected from the group consisting of $C_{1-3}$ alkyl, halo, amino, alkylamino, dialkylamino, hydroxy, $C_{1-3}$ alkoxy, cyano, trifluoromethyl, and methylthio groups. Examples of suitable $R^3$ groups include phenyl optionally substituted by one or two groups selected from halogen (e.g. fluorine, chlorine or bromine), hydroxy, $C_{1-3}$ alkoxy (e.g. methoxy), $C_{1-4}$ alkyl (e.g., methyl, ethyl, t-butyl, and haloalkyls such as trifluoromethyl), and cyano. Also, $R^3$ can be $C_{5-7}$ cycloalkyl (e.g., cyclohexyl), $C_{5-7}$ cycloalk-2-en-1-yl (e.g., cyclohex-2-en-1-yl or cyclopent-2-en-1-yl), or $C_{3-6}$ alk-2-en-1-yl (e.g., 3-methyl-prop-2-en-1-yl or 2-methyl-prop-2-en-yl). Preferably, the group $R^3$ is phenyl or a substituted phenyl group; and most preferably $R^3$ is phenyl.

Examples of suitable preferred compounds according to the invention include those described in the Examples herein.

Specifically, most preferred compounds of the invention include: 3-[3-methoxy-4-(2-pyrrolidin-1-yl-ethyl)-phenyl]-7-phenyl-3H-benzo[d][1,2,3]triazin-4-one; 3-[3-methoxy-4-(2-pyrrolidin-1-yl-ethoxy)-phenyl]-6-phenyl-3H-thieno[3,2-d]pyrimidin-4-one; and physiologically acceptable acid addition salts thereof.

The compounds of formula (I) form acid addition salts and can be dosed as such. For use in medicine acid addition salts of a compound of formula (I) will be those formed with physiologically acceptable inorganic and organic acids. Examples of such suitable acids include hydrochloric, hydrobromic, phosphoric, acetic, ascorbic, benzoic, citric, fumaric, lactic, maleic, mandelic, methanesulphonic, salicylic, succinic, and tartaric.

Other acid addition salts of the compounds of formula (I) may however be useful in the preparation and/or isolation of a compound of formula (I) or a physiologically acceptable salt thereof and are contemplated as being part of the invention herein.

Compounds of the present invention are antagonists of a human 11CBy receptor disclosed in Nature, 400, 261–265 (1999). Accordingly, these compounds are believed to have a role in the treatment (preventing, prophylaxis, ameliorating, or correcting) of dysfunctions or diseases, including, but not limited to, infections such as bacterial, fungal, protozoan and viral infections, particularly infection caused by HIV-1 or HIV-2; pain; cancers; diabetes; obesity; feeding abnormalities, such as anorexia and bulimia; drinking abnormalities (too much or too little liquid consumption); asthma; Parkinson's disease; both acute and congestive heart failure; hypertension; urinary retention; osteoporosis; angina pectoris; myocardial infarction; ulcers; allergies; benign prostatic hypertrophy; psychotic and neurological disorders, including anxiety, schizophrenia, depression (major), manic depression (bi-polar depression), delirium, dementia, and/or severe mental retardation; and dyskinesias (such as Huntington's disease or Gilles de la Tourette's syndrome, among others), hereinafter all of the above conditions (diseases, dysfunctions, abnormalities, etc.) are referred to collectively herein as "the Disorders". Preferably, this aspect of the invention provides for the treatment (including prophylaxis) of one or more of the Disorders selected from diabetes, major depression, manic depression (bipolar disorder), anxiety, schizophrenia and sleep disorders. Preferred among these disorders are obesity, diabetes (especially diabetes mellitus), major depression, and anxiety.

It has been reported that over-expression of MCH gene in mouse is associated with obesity and insulin resistance (Ludwig D S et al. Melanin-concentrating hormone overexpression in transgenic mice leads to obesity and insulin resistance. J Clin Invest 2001 107(3): 379–386). In vitro data revealed that MCH stimulates insulin secretion in both CRI-G1 and RINm5F cell-lines (Tadayyon M et al. Expression of melanin-concentrating hormone receptors in insulin-producing cells: MCH stimulates insulin release in RINm5F and CRI-G1 cell-lines. BBRC 2000 275: 709–712).

In this patent we also disclose that surprisingly MCH contributes to blood glucose regulation by increasing plasma glucagon levels in conscious instrumented rats. In addition, we claim the use of 11CBy antagonists to inhibit MCH-induced hyperglycemia by reducing MCH-induced hyperglucagonemia. Thus, in addition to other important impications of 11CBy antagonists in obesity and neurological indications, such antagonists will have therapeutic implication for the treatment of diabetes mellitus.

The administration of such compounds to a mammal may be by way of oral (including sub-lingual), parenteral, nasal, rectal or transdermal administration. An amount effective to treat the Disorders herein before described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that compounds of formula (I) and or physiologically acceptable salts or solvates thereof are administered in the form of a unit-dose composition, such as a unit dose oral (including sub-lingual), nasal, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats; emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and is sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Compounds of the present invention may be employed alone or in conjunction with other compounds, such as therapeutic compounds.

No adverse toxicological effects are expected for the compounds of the invention, when administered in accordance with the invention.

Accordingly, in a further aspect, the present invention provides a pharmaceutical composition for use in the treatment and/or prophylaxis of one or more of the Disorders which comprises a compound of this invention, or a physiologically acceptable salt or solvate thereof, and a pharmaceutically acceptable carrier.

The present invention also provides a method of treatment and/or prophylaxis of one or more of the Disorders comprising administering to the sufferer in need thereof an effective or prophylactic amount of a compound of this invention, or a physiologically acceptable salt or solvate thereof.

In a further aspect the invention provides the use of a compound of this invention, or a physiologically acceptable salt or solvate thereof, for the manufacture of a medicament for the treatment and/or prophylaxis of one or more of the Disorders. In a still further aspect the invention provides a compound of formula (I), or a physiologically acceptable salt or solvate, thereof as a therapeutic agent, in particular for the treatment and/or prophylaxis of one or more of the Disorders.

A further aspect of the invention provides processes for the preparation of compounds of formula (I). Unless stated otherwise, $R^1$, $R^2$, $R^3$, $R^6$, Z, Q, Y, M, and L are as defined in formula (I).

Thus compounds of formula (I) wherein Y is a 5 membered ring containing two carbonyl groups may be prepared by reaction of an aniline of formula (II)

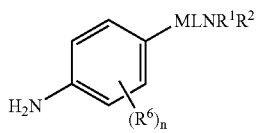

wherein $R^6$, n, M, L, $R^1$ and $R^2$ have the meanings defined in formula (I) or are protected derivatives thereof with appropriate anhydride (III), orthodicarboxylic acid (IV) or imide (V) set forth below

wherein $R^3$, Z and Q have the meanings defined in formula (I), under conventional conditions for the formation of the required imide group Y.

The reaction is carried out using a coupling agent, e.g., dicyclohexylcarbodiimide, conveniently on a resin support, in an appropriate solvent such as a halohydrocarbon, e.g., dichloromethane or an amide such as N,N-dimethylformamide or a mixture thereof and optionally in the presence of a tertiary organic base such as 4-dimethylaminopyridine or diethylisopropylamine, which is also conveniently on a resin support.

Compounds of formula (I) where Y is a 5-membered ring containing a single carbonyl group may be prepared by reduction of the corresponding compound of formula (I) wherein Y is a 5 membered ring containing 2 carbonyl groups, using a conventional two step reduction process. For example, reduction with a suitable hydride such as a borohydride followed by treatment with a hydrogen donor such as triethylsilane in the presence of a suitable acid, e.g., trifluoroacetic acid.

Compounds of formula (I) wherein Y is a 6-membered heterocycle may be prepared by cyclisation of the compound of formula (VI)

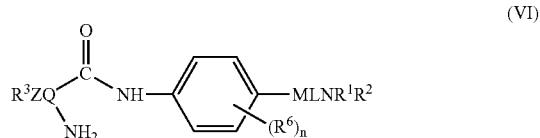

wherein $R^3$ Z, Q, $R^6$, n, M, L, $R^1$ and $R^2$ have the meanings defined in formula (I). Thus compounds of formula (I) wherein Y is a pyrimidin-4-one moiety may be prepared by heating a compound of formula (VI) with formic acid or an appropriate orthoester e.g. triethylorthoformate in a suitable solvent such as a halohydrocarbon e.g. dichloroethane followed by treatment with a strong base such as 1,8-diazabicyclo[5.4.0]undec-7-one (DBU).

Compounds of formula (I) wherein Y is a pyrimidine-2, 4-dione may be prepared by treating the amine (VI) with a carboxylating agent such as carbonyl-diimidazole and a strong base such as DBU in a suitable aprotic solvent such as dichloroethane.

Compounds of formula (I) wherein Y is a 1,2,3-triazin-4-one may be prepared by diazotisation of the compound of formula (VI) followed by treatment with a strong base, e.g. DBU. Thus, the reaction may be carried out by reacting a solution of amine (VI) in a solvent such as dichloromethane with an alkyl nitrite, e.g., butyl or amyl nitrite, in the presence of a suitable organic carboxylic acid, e.g., trifluoroacetic acid followed by addition of the strong base.

Compounds of formula (I) wherein Y is a pyrimidine ring containing a thiocarbonyl group or an alkylthio substituent at the 2 position may be prepared from the thiourea (VII)

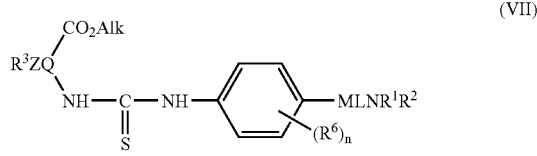

(VII)

wherein $R^3$, Z, Q, $R^6$, n, M, L, $R^1$ and $R^2$ have the meanings defined in formula (I) or are protected derivatives thereof and Alk is $C_{1-4}$alkyl. Thus, compounds of formula (I) wherein Y contains a 2-thiocarbonyl group may be prepared by heating the thiourea (VII) in a suitable high boiling solvent such as an aromatic hydrocarbon, e.g., toluene.

Compounds of formula (I) wherein Y is a pyrimidinone having an alkylthio group at the 2 position may be prepared by reaction of compound (VII) with the appropriate alkyl halide in an aprotic polar solvent such as DMF and in the presence of a suitable base such as a tertiary amine or an alkali or alkaline metal earth carbonate, e.g., sodium carbonate or potassium carbonate.

Compounds of formula (I) wherein Y is a pyridmidinone derivative, unsubstituted at the 2-position maybe prepared from the corresponding pyrimidinone having an alkylthio group at the 2-position by reaction with Raney nickel in a solvent such as an alkanol, e.g., ethanol.

Compounds of formula (I) may also be prepared by reaction of a compound of formula (VIII)

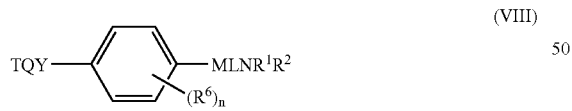

(VIII)

wherein Q, Y, $R^6$, n, M, L, $R^1$ and $R^2$ have the meanings defined in formula (I) or a group convertible thereto and T is a leaving or displacable group, e.g., halogen, with a compound capable of introducing the group $R^3Z$.

Thus, compounds of formula (I) wherein Z is a bond and $R^3$ is an aryl group may be prepared from the halide of formula (VIII) with the appropriate arylboronic acid using a Suzuki coupling reaction or with the appropriate aryl-tin reagent using a Stille displacement reaction.

Compounds of formula (I) wherein Z is a methylene group may be prepared by treating a compound of formula (VIII) with an appropriate organo zinc or organo magnesium compound in the presence of a palladium catalyst. The reaction is carried out in an aprotic solvent such as an ether (e.g., THF) and the organo zinc or organo magnesium compound is one capable of introducing the group $R^3CH_2$.

Compounds of formula (I) wherein Z is NH or $NCH_3$ may be prepared by reacting the halide of formula (VIII) with the appropriate amine $R^3NH_2$ or $R^3NHCH_3$ in the presence of a palladium catalyst under standard Buchwald conditions.

Compounds of formula (I) wherein Z is sulphur may be prepared by reaction of a compound of formula (VIII) with the thiol $R^3SH$ in the presence of a suitable base such as an alkali metal hydride in an aprotic solvent such as an ether, e.g., THF. Similarly, compounds of formula (I) wherein Z is oxygen may be prepared by the reaction of the compound of formula (VIII) with the compound $R^3OH$ in the presence of an alkali metal hydride and an aprotic solvent, e.g., DMF.

The anilines of formula (II) are either known compounds or may be prepared by analogous methods described for preparing the known compounds. Thus, compounds of formula (II) wherein L and $(R^6)_n$ are to form a cyclic group as defined in formula (I) may be prepared using the procedures described in WO 01/2577 A2.

Compounds of formula (II) wherein M is O or S may be prepared by reaction of the nitrochlorobenzene (X)

(X)

wherein $R^6$ and n has the meanings defined in formula (I) or is a group convertible thereto, with the compound (XI)

$HMLNR^1R^2$ (XI)

wherein M is O or S and L, $R^1$ and $R^2$ have the meaning defined in formula (I) or $R^1$ and $R^2$ are protected derivatives thereof, in the presence of a strong base such as sodium hydride in a polar aprotic solvent such as DMF, followed by reduction of the nitro group to amino using conventional means such as hydrogen and a palladium catalyst or iron and ammonium chloride.

Compounds of formula (II) wherein M is $CH_2$ may be prepared by reacting an activated derivative of the acid (XII)

(XII)

wherein $R^6$ and n have the meanings as defined in formula (I) and $L_1$ is a 1 or 2 membered alkylene chain with the amine $HNR^1R^2$ wherein $R^1$ and $R^2$ have the meanings defined in formula (I) followed by reduction of the resultant amide with borane in an aprotic solvent such as tetrahydrofuran and then reduction of the nitro group using conventional procedures as documented above.

Alternatively compounds of formula (I) may be prepared by alkylation of the amino $R^1R^2NH$ wherein $R^1$ and $R^2$ have the meaning defined in formula (I) or are protected derivatives thereof by reaction with a compound of formula (XIII)

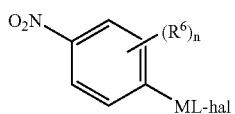

(XIII)

wherein $R^6$, n, M and L have the meanings defined in formula (I) and hal is a halogen in the presence of a suitable base and a polar solvent such as DMF, and subsequent generation of the required primary amino group by reaction of the corresponding nitro group using a conventional procedure.

The compounds of formula (X), (XI), (XII) and (XIII) are either known compounds or may be prepared by analogous methods to those used to prepare the known compounds.

The anhydride (III) is either a known compound or may be prepared by analogous methods to those described for preparing known compounds. Thus the compounds may be prepared from the anhydride (IX)

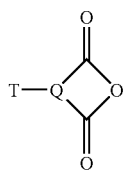

(IX)

wherein Q has the meaning in formula (I) and T is a leaving group, using the same reaction conditions to introduce the group $R^3Z$ as described above for the preparation of compounds of formula (I) from the compounds of formula (VIII).

The ortho dicarboxylic acid (IV) and the imide (IV) may also be prepared in an analogous manner to that for preparing the anhydride (III) from the compound of formula (IX).

Compounds of formula (VI) may be prepared by the process outlined below wherein

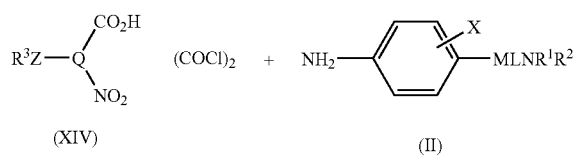

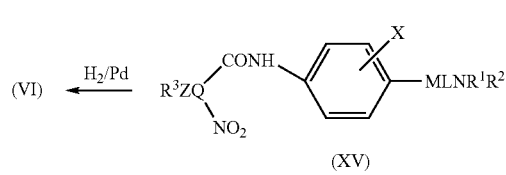

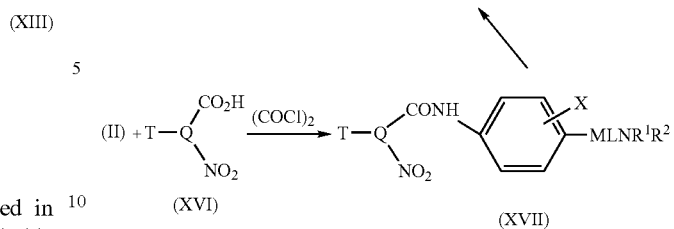

In the above formulae the groups M, L, $R^1$, $R^2$, $R^3$, $R^6$, n, Z and Q have the meaning defined in formula (I) and T is a displaceable group as defined in formula (VIII).

The condensation of an activated derivative, e.g., acid chloride of the acids (XIV) or (XVI) with the amine (II) to give amides (XV) and (XVII) may be carried out under conventional conditions for preparing amides from anilines and a carboxylic acid.

Compounds of formula (XVII) may be converted into the required compound (XV) using the conditions described above for converting a compound of formula (VIII) into a compound of formula (I).

The carboxylic acid (XIV) may be prepared from the corresponding carboxylic acid (XVI) or a protected derivative thereof by the conditions previously described above for introducing the group $R^3Z$ by displacement of the group T.

Alternatively, compounds of formula (VI) may be prepared by the process outlined below wherein $R^1$, $R^2$, $R^3$, $R^6$, Z, Q, M, and L are as defined in formula (I).

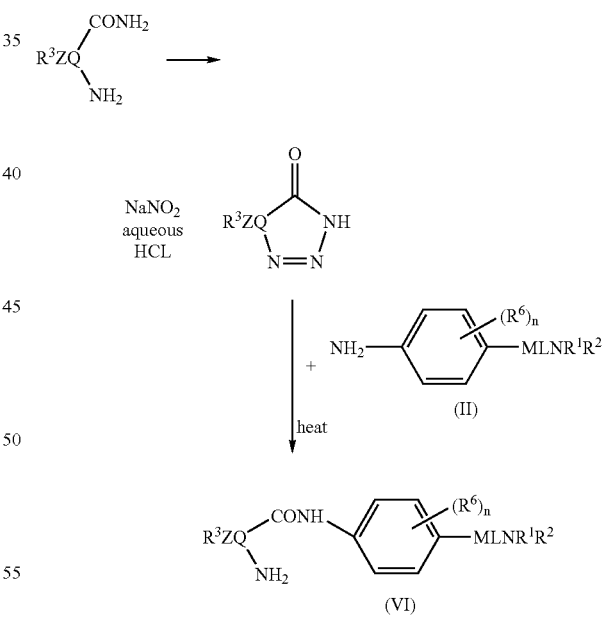

Compounds of formula (VII) may be prepared by the process as outlined below wherein $R^1$, $R^2$, $R^3$, $R^6$, Z, Q, M, and L are as defined in formula (I), and Alk is $C_{1-4}$ alkyl.

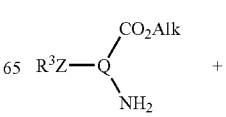

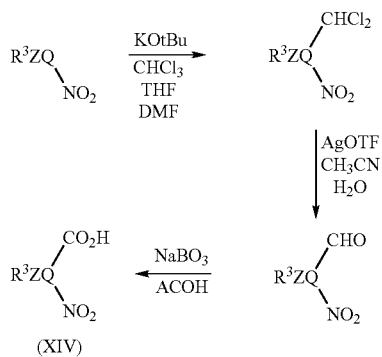

Compounds of formula (VIII) may be prepared from the aniline (II) and the anhydride (IX) or carboxylic acid (XVI) using the general processes described above for preparing the corresponding compounds of formula (I) from the aniline (II).

The acids of formula (XIV) are either known compounds or can be prepared by analogous processes to those used for preparing the known compounds. Alternatively, they may be prepared by the process outlined below wherein wherein $R^3$, Z, and Q are as defined in formula (I).

In the above processes, it will be appreciated that it may be necessary to carry out the reactions wherein one or more of the groups $R^3$, Z, Q, X, M, L, $R^6$, $R^1$ or $R^2$ may need to be present in a protected form and then the protecting group(s) removed. The need for such protection will be well understood by those skilled in the art and such protection is clearly within the scope of the present invention.

Acid addition salts of compounds of formula (I) may be prepared in a conventional manner by treating the compound of formula (I) with the appropriate inorganic or organic acid. For example, by addition of the acid, optionally as a solution in an organic solvent to a solution of the free base in a suitable solvent.

Compounds for use in this invention and their preparation are illustrated in the following Examples and Tables.

These Examples illustrate general procedures and sources of chemicals utilised to prepare compounds whose structures are shown in the Tables of data which follow the Examples. In the case of Examples prepared as members of a coupled array, the synthetic origin of all starting components of the array are shown in the Examples. Rather than detailing the experimental procedure for each case, the method by which individual members of the array were prepared is indicated in a Table by reference to a related Example. Mass spectral characterisation of all Examples is provided in the tables of data. Additional characterisation is provided for selected representative Examples with full experimental procedures.

EXAMPLE A1

2-[4-(2-Diisopropylamino-ethoxy)-3-methoxy-phenyl]-5-phenyl-isoindole-1,3-dione

4-Bromophthalic anhydride [Apin] (2.27 g, 10 mmol) was dissolved in 1,2-dichloromethane (8 ml), and pyridine (10 mmol, 0.81 ml) was added, followed by 4-(2-diisopropylamino-ethoxy)-3-methoxy-phenylamine [Patent WO-9901127] (2.44 g, 10 mmol) and a catalytic amount of 4-dimethylaminopyridine [Aldrich]. The mixture was heated for 16 h at 85° C. The mixture was evaporated in vacuo and applied to a Biotage Flash40M cartridge, (eluting with dichloromethane-methanol-aqueous ammonia) to give the 5-bromo-2-[4-(2-diisopropylamino-ethoxy)-3-methoxyphenyl]-isoindole-1,3-dione 3.05 g, 68%, as the trifluoroacetate salt;

$^1$H NMR (CDCl$_3$): δ 1.06 (12H, bd), 2.92 (2H, bt), 3.05 (2H, bm), 3.88 (3H, s), 3.99 (2H, bt), 6.89–7.03 (3H, m), 7.78 (1H, d), 7.91 (1H, dd) 8.06 (1H, d); m/z [AP+] 475, 477 (M+H$^+$, 100%).

A solution of this material (331 mg, 0.7 mmol) in benzene (46 ml), ethanol (9 ml) and aqueous sodium carbonate (2M, 9 ml) was degassed and treated with phenyl boronic acid (85 mg, 0.7 mmol) and tetrakis(triphenylphosphine)palladium [0] (20 mg). The mixture was brought to reflux (80° C.) for 16 hours then cooled and filtered through filter-aid, washing with dichloromethane. The filtrate was evaporated and the residue subjected to flash chromatography on silica gel (eluting with methanol-dichloromethane-aqueous amnonia) to obtain the title compound;

$^1$H NMR (CDCl$_3$): δ 1.06 (12H, d), 2.94 (2H, t), 3.07 (2H, m), 3.89 (3H, s), 4.00 (2H, t), 6.95–7.00 (3H, m), 7.35–7.52 (3H, m), 7.67 (2H, dd), 7.99 (2H, s), 8.15 (1H, s), which crystallised on treatment with 1M HCl in ether to a white solid.

EXAMPLE A2

5-Benzyl-2-[4-(2-diisopropylamino-ethoxy)-3-methoxy-phenyl]-isoindole-1,3-dione

A mechanically agitated piece of zinc foil [Aldrich] (99.99%, 0.1 mm thick, 0.5 g), in dry THF under argon was treated with trimethylsilyl chloride (20 ul), then after ten minutes, 1,2-dibromoethane (80 ul). The mixture was stirred for 20 minutes then a solution of benzyl bromide (5 mmol, 0.59 ml) and THF (4.4 ml) introduced. The mixture was stirred at 0° C. for 2 h then warmed to RT for 16 h. A 2.6 ml portion of the resulting solution was added to a mixture of 5-bromo-2-[4-(2-diisopropylamino-ethoxy)-3-methoxyphenyl]-isoindole-1,3-dione [Example A1], tetrakis(triphenylphosphine)palladium[0] (5 mol %, 120 mg), and THF (3 ml). The mixture was heated at 60° C. for 16 h. The resulting solution was evaporated and partially purified by flash chromatography (dichloromethane-methanol-aqueous ammonia) on silica gel before being further purified by reverse phase chromatography (aq. MeCN/TFA) to give the title compound as the trifluoroacetate salt;

$^1$H NMR (CDCl$_3$): δ 1.45 (12H, m), 3.52 (2H, t), 3.84 (2H, s), 3.85 (3H, sm), 4.15 (2H, m), 4.74 (2H, t), 5.80 (1H, bs), 6.92–7.04 (3H, m), 7.19–7.35 (5H, m), 7.60 (1H, dd), 7.75 (1H, s), 7.83 (1H, d).

EXAMPLE A3

2-[4-(2-Diisopropylamino-ethoxy)-3-methoxy-phenyl]-5-phenylamino-isoindole-1,3-dione A mixture of palladium II acetate (7.5 mg, 0.04 mmol), 2-(dicyclohexylphosphino)biphenyl [Digital] (0.06 mmol, 21 mg) and cesium carbonate (205 mg, 0.63 mmol) in 1,4-dioxane (5 ml) was sonicated under argon for 40 minutes. To this suspension was added a mixture of 5-bromo-2-[4-(2-diisopropylamino-ethoxy)-3-methoxy-phenyl]-isoindole-1,3-dione [Example A1] (200 mg, 0.42 mmol) and aniline (0.42 mmol, 39 mg) in 1,4-dioxane (1 ml). The mixture was heated at 85° C. for 16 h then the cooled mixture filtered through filter-aid and the filtrate evaporated. The residue was subjected to purification by preparative reverse phase chromatography (aq. MeCN, TFA) to give the title compound as the trifluoroacetate salt;

$^1$H NMR (CDCl$_3$): δ 1.46 (12H, m), 3.51 (2H, t), 3.80–3.87 (2H, m), 3.86 (3H, s), 4.50 (2H, t), 6.4 (1H, bs), 6.94–7.03 (3H, m), 7.17–7.24 (4H, m), 7.38–7.44 (3H, m), 7.75 (1H, d).

EXAMPLE A4

2-[3-Methoxy-4-(2-pyrrolidin-1-yl-ethoxy)-phenyl]-5-phenoxy-isoindole-1,3-dione hydrochloride To a solution of the 1-(2-hydroxyethyl)-pyrrolidine [Aldrich], (1.87 ml, 16 mmol) in dimethylformamide was added portionwise sodium hydride [60% dispersion in oil, (544 mg, 16 mmol). After stirring at room temperature for 10 minutes a solution of 1-chloro-2-methoxy-4-nitro-benzene [Avocado] (3 g, 16 mmol) in dimethylformamide (10 ml) was added dropwise. The reaction mixture was left stirring at room temperature for 16 hrs then concentrated. The residue was dissolved in ethyl acetate (200 ml) and washed with water (3×50 ml). The organic phase was dried with magnesium sulphate, evaporated and the residue purified by flash chromatography on silica gel using dichloromethane-aq. ammonia-methanol as eluent to afford 1-[2-(2-methoxy-4-nitro-phenoxy)-ethyl]-pyrrolidine as a brown oil.

$^1$H NMR (CDCl$_3$): δ1.82 (4H, m), 2.65 (4H, m), 3.01 (2H, t), 3.94 (3H, s), 4.24 (2H, t), 6.92 (1H, d), 7.74 (1H, d), and 7.89 (1H, dd); MS (AP+ve): m/z 267 [M+H]$^+$.

To a solution of 1-[2-(2-methoxy-4-nitro-phenoxy)-ethyl]-pyrrolidine (2.3 g, 8.6 mmol) in ethanol (100 ml) was added 10% Pd/C (50 mg). The mixture was stirred at room temperature under an atmosphere of hydrogen at atmospheric pressure for 16 h, then filtered through celite and the filtrate concentrated to give the corresponding aniline; 3-methoxy-4-(2-pyrrolidin-1-yl-ethoxy)-phenylamine, as a brown solid.

$^1$H NMR (CDCl$_3$): δ 1.80 (4H, m), 2.62 (4H, m), 2.89 (2H, t), 3.5 (2H, brs), 3.80 (3H, s), 4.06 (2H, t), 6.20 (1H, dd), 6.29 (1H, d) and 6.75 (1H d); MS (AP+ve): m/z 237 [M+H]$^+$.

4-Phenoxy-phthalic acid [J. Org. Chem. (1977), 42(21), 3425–31] (893 mg, 3.5 mmol) was dissolved in DMF (30 ml) and polymer bound N-cyclohexylcarbodiimide [Argonaut Technologies] (1.69 mol. eq./g, 4.1 g) was added, followed by a solution of 3-methoxy-4-(2-pyrrolidin-1-yl-ethoxy)-phenylamine (817 mg, 3.5 mmol) in DMF (5 ml) and a catalytic amount of DMAP. The mixture was stirred for 16 h at ambient temperature. The resin was filtered off over filter-aid, washing with dichloromethane. The filtrate was evaporated in vacuo and purified by chromatography using a Biotage Flash40M cartridge (eluting with dichloromethane-methanol-aqueous ammonia). The resulting yellow oil was dissolved in CHCl$_3$ and treated with ethereal HCl (1 M, 2 ml) to give a yellow solid. Recrystallisation from methanol/diethyl ether gave the title compound as an off-white solid (328 mg, 0.7 mmol);

$^1$H NMR (CDCl$_3$): δ 12.82 (1H, br), 7.88 (1H, dd), 7.45–7.27 (5H, m), 7.13–6.94 (5H, m), 4.57 (2H, t), 3.91 (2H, br), 3.86 (3H, s), 3.50 (2H, br), 3.07 (2H, br), 2.26–2.07 (4H, m, br).

EXAMPLE A5

2-[3-Methoxy-4-(2-pyrrolidin-1-yl-ethoxy)-phenyl]-5-phenylamino-isoindole-1,3-dione 3-Methoxy-4-(2-pyrrolidin-1-yl-ethoxy)-phenylamine [Example A4] was used in the same manner as 4-(2-diisopropylamino-ethoxy)-3-methoxy-phenylamine in the procedure of Example A1 to form 5-bromo-2-[3-methoxy-4-(2-pyrrolidin-1-yl-ethoxy)-phenyl]-isoindole-1,3-dione;

$^1$H NMR (CDCl$_3$): δ 2.05 (4H, m), 3.15 (4H, bs), 3.32 (2H, t), 3.87 (3H, s), 4.43 (2H, t), 6.92–7.06 (3H, m), 7.80 (1H, d), 7.92 (1H, dd), 8.07 (1H, d).

This material was used in the procedure of Example A3 in place of 5-bromo-2-[4-(2-diisopropylamino-ethoxy)-3-methoxy-phenyl]-isoindole-1,3-dione to afford the title compound as a trifluoroacetate salt;

$^1$H NMR (CDCl$_3$): δ 2.12 (4H, bd), 2.5 (1H, bs), 3.08 (2H, bm), 3.55 (2H, m), 3.85 (3H, s), 3.88 (2H, m), 4.12 (2H, t), 6.96 (3H, m), 7.17–7.26 (4H, m), 7.39–7.44 (3H, m), 7.73 (1H, d) 12.5 (1H, bs).

EXAMPLE A6

5-Benzyl-2-[3-methoxy-4-(2-pyrrolidin-1-yl-ethoxy)-phenyl]-isoindole-1,3-dione

5-Bromo-2-[3-methoxy-4-(2-pyrrolidin-1-yl-ethoxy)-phenyl]-isoindole-1,3-dione [Example A5] was used in the same manner as 5-bromo-2-[4-(2-diisopropylamino-ethoxy)-3-methoxy-phenyl]-isoindole-1,3-dione in the procedure of Example A2 to afford the title compound as the trifluoroacetate salt;

$^1$H NMR (CDCl$_3$): δ 2.14 (4H, bm), 3.10 (2H, m), 3.59 (2H, bt), 3.84 (3H, s), 3.91 (2H, m), 4.15 (2H, d), 4.43 (2H, t), 6.2 (1H, bs), 6.94–6.99 (3H, m), 7.18–7.74 (7H, m), 7.85 (1H, d).

EXAMPLE A7

2-[3-Methoxy-4-(2-pyrrolidin-1-yl-ethoxy)-phenyl]-5 (phenylthio)-isoindole-1,3-dione 4-Fluorophthalic anhydride [Acros] (0.84 g, 5 mmol) was dissolved in dichloromethane (30 ml) and polymer bound N-cyclohexylcarbodiimide [Argonaut Technologies] (1.69 mol. eq./g, 3 g) was added, followed by a solution of 3-methoxy-4-(2-pyrrolidin-1-yl-ethoxy)-phenylamine [Example A4] (1.18 g, 5.0 mmol) and a catalytic amount of 4-dimethylaminopyridine. The mixture was stirred for 16 h at ambient temperature. The resin was filtered off over filter-aid, and washed with dichloromethane. The filtrate was evaporated in vacuo and purified by chromatography using a Biotage Flash40M cartridge, eluting with dichloromethane-methanol to give the 5-fluoro-2-[3-methoxy-4-(2-pyrrolidin-1-yl-ethoxy)-phenyl]-isoindole-1,3-dione;

$^1$H NMR (CDCl$_3$): δ 2.12 (4H, m), 3.32 (4H, bs), 3.44 (2H, t), 3.86 (3H, s), 4.48 (2H, t), 6.93–7.03 (3H, m), 7.45 (1H, dt), 7.60 (1H, dd), 7.90 (1H, dd); m/z [AP+] 458 (M+H$^+$, 100%).

A portion of this material (96 mg, 0.25 mmol) was added to a stirred mixture of thiophenol (55 mg, 0.5 mmol) and sodium hydride (60% oil dispersion, 16 mg/0.4 mmol) in DMF (2 ml) and the mixture warmed to 50° C. The solution was cooled, evaporated and the residue purified by reverse phase chromatography (acetonitrile-water-TFA) to give the title compound as the trifluoroacetate salt, an off white solid;

$^1$H NMR (CDCl$_3$): δ 1.85 (4H, m), 2.74 (4H, m), 3.02 (2H, t), 3.85 (3H, s), 4.22 (2H, t), 6.89–6.97 (3H, m), 7.44–7.60 (7H, m), 7.76 (1H, d).

EXAMPLE A8

5-[(4-chlorophenyl)thio]-2-[3-methoxy-4-(2-pyrrolidin-1-ylethoxy)phenyl]-1H-isoindole-1,3(2H)-dione Using the method of Example A7 but utilising 4-chlorothiophenol [Aldrich] in place of thiophenol to give the title compound as the trifluoroacetate salt.

EXAMPLE A9

5-[(3-methoxyphenyl)thio]-2-[3-methoxy-4-(2-pyrrolidin-1-ylethoxy)phenyl]-1H-isoindole-1,3(2H)-dione Using the method of Example A7 but utilising 3-methoxythiophenol [Aldrich] in place of thiophenol to give the title compound as the trifluoroacetate salt.

EXAMPLE A10

5-[(4-hydroxyphenyl)thio]-2-[3-methoxy-4-(2-pyrrolidin-1-ylethoxy)phenyl]-1H-isoindole-1,3(2H)-dione Using the method of Example A7 but utilising 4-hydroxythiophenol [Aldrich] in place of thiophenol to give the title compound as the trifluoroacetate salt.

EXAMPLE A11

5-[(4-fluorophenyl)thio]-2-[3-methoxy-4-(2-pyrrolidin-1-ylethoxy)phenyl]-1H-isoindole-1,3(2H)-dione Using the method of Example A7 but utilising 4-fluorothiophenol [Aldrich] in place of thiophenol to give the title compound as the trifluoroacetate salt.

EXAMPLE A12

5[(4-aminophenyl)thio]-2-[3-methoxy-4-(2-pyrrolidin-1-ylethoxy)phenyl]-1H-isoindole-1,3(2H)-dione Using the method of Example A7 but utilising 4-aminothiophenol [Aldrich] in place of thiophenol to give the title compound as the trifluoroacetate salt.

EXAMPLE A13

2-[3-methoxy-4-(2-pyrrolidin-1-ylethoxy)phenyl]-5-{[4-(trifluoromethyl)phenyl]thio}-1H-isoindole-1,3(2H)-dione Using the method of Example A7 but utilising 4-trifluoromethylthiophenol [Aldrich] in place of thiophenol to give the title compound as the trifluoroacetate salt.

EXAMPLE A14

5-[(4-methoxyphenyl)thio]-2-[3-methoxy-4-(2-pyrrolidin-1-ylethoxy)phenyl]-1H-isoindole-1,3(2H)-dione Using the method of Example A7 but utilising 4-methoxythiophenol [Aldrich] in place of thiophenol to give the title compound as the trifluoroacetate salt.

EXAMPLE A15

5-(4-Chloro-phenoxy)-2-[3-methoxy-4-(2-pyrrolidin-1-yl-ethoxy)-phenyl]-isoindole-1,3-dione 4-Fluorophthalic anhydride (42 mg, 0.25 mmol) in DMF (0.5 ml) was treated with 4-chlorophenol (32 mg, 0.25 mmol) and sodium hydride (60% oil disp. 10 mg, 0.25 mmol). The mixture was heated to 140° C. for 15 minutes then cooled, dichloromethane (5 ml) added, 3-methoxy-4-(2-pyrrolidin-1-yl-ethoxy)-phenylamine [Example A4] (59 mg, 0.25 mmol) introduced, polymer bound N-cyclohexylcarbodiimide (1.69 mol. eq./g, 0.5 g) added, polymer bound diethylisopropylamine resin [Argonaut Technologies] (3.49 mol. eq./g, 0.2 g) added and the mixture stirred at RT for 16 hours. The solution was filtered through filter-aid, washing with dichloromethane, the combined organic phases evaporated and purified by reverse phase chromatography (acetonitrile-water-TFA) to give the title compound as its trifluoroacetate salt;

$^1$H NMR (CDCl$_3$): δ 2.1 (2H, bs), 2.25 (2H, bs), 3.05 (2H, bs), 3.55 (2H, bs), 3.83 (3H, s), 3.89 (2H, bs), 4.55 (2H, bs) 6.97–7.19 (5H, m), 7.39 (1H, d), 7.47 (1H, s), 7.70 (2H, d), 7.93 (1H, d), 12.7 (1H, bs).

19

EXAMPLE A16

5-(4-fluorophenoxy)-2-[3-methoxy-4-(2-pyrrolidin-1-ylethoxy)phenyl]-1H-isoindole-1,3(2H)-dione 5-Nitro-2-phenylisoindole-1,3-dione (5.9 g, 22 mmol) was dissolved in DMF (40 ml) and sodium 4-fluorophenolate (3.1 g, 23.1 mmol) was added. The resulting mixture was stirred at 100° C. for 2 hours under an argon atmosphere. The mixture was allowed to cool to RT then poured into 4% aqueous HCl. The yellow precipitate which formed was filtered off, washed with water and recrystallised (DCM/TBME) to yield (4-fluorophenoxy)-2-phenylisoindol-1,3-dione (2.4 g, 41%);

MS [APCI$^+$] 334 (100%, M+H$^+$).

This phthalimide (1.4 g, 4.2 mmol), ethyleneglycol (20 mL) and 25% aqueous NaOH (4 mL) were heated at 140° C. for 16 hours. The resulting mixture was poured into 1M aqueous HCl to give an orange precipitate. This was washed with 0.1 M aqueous HCl and water then dried to afford 4-(4-fluorophenoxy)phthalic acid in 65% yield; m/z [APCI$^-$] 275 (20%, M−H$^-$), 231 (100%).

Using the procedure of Example A4 but utilising 4-(4-fluorophenoxy)phthalic acid in place of 4-phenoxyphthalic acid gave the title compound which crystallised from ethereal hydrochloric acid to give a white solid.

Also by the method of Example A15 but using 4-fluorophenol in place of 4-chlorophenol to give the title compound as the trifluoroacetate salt.

EXAMPLE A17

5-(4-Trifluoromethyl-phenoxy)-2-[3-methoxy-4-(2-pyrrolidin-1-yl-ethoxy)-phenyl]-isoindole-1,3-dione Using the method of Example A15 but utilising 4-trifluoromethylphenol [Aldrich] in place of 4-chlorophenol to give the title compound as the trifluoroacetate salt.

EXAMPLE A18

5-(4-Fluoromethyl-phenoxy)-2-[3-methoxy-4-(2-pyrrolidin-1-yl-ethoxy)-phenyl]-isoindole-1,3-dione Using the method of Example A15 but utilising 4-fluoro-3-chlorophenol [Aldrich] in place of 4-chlorophenol to give the title compound as the trifluoroacetate salt.

EXAMPLE A19

5-(3-Fluoro-phenoxy)-2-[3-methoxy-4-(2-pyrrolidin-1-yl-ethoxy)-phenyl]-isoindole-1,3-dione Using the method of Example A15 but utilising 3-fluorophenol [Aldrich] in place of 4-chlorophenol to give the title compound as the trifluoroacetate salt.

EXAMPLE A20

5-(3-Chloro-phenoxy)-2-[3-methoxy-4-(2-pyrrolidin-1-yl-ethoxy)-phenyl]-isoindole-1,3-dione Using the method of Example A15 but utilising 3-chlorophenol [Aldnrch] in place of 4-chlorophenol to give the title compound as the trifluoroacetate salt.

20

EXAMPLE A21

5-(3-tert-Butyl-phenoxy)-2-[3-methoxy-4-(2-pyrrolidin-1-yl-ethoxy)-phenyl]-isoindole-1,3-dione Using the method of Example A15 but utilising 3-tert-butylphenol [Aldrich] in place of 4-chlorophenol to give the title compound as the trifluoroacetate salt.

EXAMPLE A22

5-(3-Methoxy-phenoxy)-2-[3-methoxy-4-(2-pyrrolidin-1-yl-ethoxy)-phenyl]-isoindole-1,3-dione Using the method of Example A15 but utilising 3-methoxyphenol [Aldrich] in place of 4-chlorophenol to give the title compound as the trifluoroacetate salt.

EXAMPLE A23

5-(3-Methyl-phenoxy)-2-[3-methoxy-4-(2-pyrrolidin-1-yl-ethoxy)-phenyl]-isoindole-1,3-dione Using the method of Example A15 but utilising 3-methylphenol [Aldrich] in place of 4-chlorophenol to give the title compound as the trifluoroacetate salt.

EXAMPLE A24

5-(4-Methyl-phenoxy)-2-[3-methoxy-4-(2-pyrrolidin-1-yl-ethoxy)-phenyl]-isoindole-1,3-dione Using the method of Example A15 but utilising 4-methylphenol [Aldrich] in place of 4-chlorophenol to give the title compound as the trifluoroacetate salt.

EXAMPLE A25

5-(4-Cyano-phenoxy)-2-[3-methoxy-4-(2-pyrrolidin-1-yl-ethoxy)-phenyl]-isoindole-1,3-dione Using the method of Example A15 but utilising 4-cyanophenol [Aldrch] in place of 4-chlorophenol to give the title compound as the trifluoroacetate salt.

EXAMPLE A26

5-(2-Cyano-phenoxy)-2-[3-methoxy-4-(2-pyrrolidin-1-yl-ethoxy)-phenyl]-isoindole-1,3-dione Using the method of Example A15 but utilising 2-cyanophenol [Aldrich] in place of 4-chlorophenol to give the title compound as the trifluoroacetate salt.

EXAMPLE A27

2-[3-methoxy-4-(2-pyrrolidin-1-ylethoxy)phenyl]-5-[2-(methylthio)phenoxy]-1H-isoindole-1,3(2H)-dione Using the method of Example A15 but utilising 2-(methylthio)phenol [Aldrich] in place of 4-chlorophenol to give the title compound as the trifluoroacetate salt.

EXAMPLE A28

5-(2-Bromo-phenoxy)-2-[3-methoxy-4-(2-pyrrolidin-1-yl-ethoxy)-phenyl]-isoindole-1,3-dione Using the method of Example A15 but utilising 2-bromophenol [Aldrich] in place of 4-chlorophenol to give the title compound as the trifluoroacetate salt.

EXAMPLE A29

5-(2-Chloro-phenoxy)-2-[3-methoxy-4-(2-pyrrolidin-1-yl-ethoxy)-phenyl]-isoindole-1,3-dione Using the method of Example A15 but utilising 2-chlorophenol [Aldrich] in place of 4-chlorophenol to give the title compound as the trifluoroacetate salt.

EXAMPLE A30

5-(2-Fluoro-phenoxy)-2-[3-methoxy-4-(2-pyrrolidin-1-yl-ethoxy)-phenyl]-isoindole-1,3-dione Using the method of Example A15 but utilising 2-fluorophenol [Aldrich] in place of 4-chlorophenol to give the title compound as the trifluoroacetate salt.

EXAMPLE A31

5-(2-Ethyl-phenoxy)-2-[3-methoxy-4-(2-pyrrolidin-1-yl-ethoxy)-phenyl]-isoindole-1,3-dione Using the method of Example A15 but utilising 2-ethylphenol [Aldrich] in place of 4-chlorophenol to give the title compound as the trifluoroacetate salt.

EXAMPLE A32

5-(2-,5-Difluorophenoxy)-2-[3-methoxy-4-(2-pyrrolidin-1-yl-ethoxy)-phenyl]-isoindole-1,3-dione Using the method of Example A15 but utilising 2,5-diorophenol [Aldrich] in place of 4-chlorophenol to give the title compound as the trifluoroacetate salt.

EXAMPLE A33

5-(2-Trifluoromethylphenoxy)-2-[3-methoxy-4-(2-pyrrolidin-1-yl-ethoxy)-phenyl]-isoindole-1,3-dione Using the method of Example A15 but utilising 2-trifluoromethylphenol [Aldrich] in place of 4-chlorophenol to give the title compound as the trifluoroacetate salt.

EXAMPLE A34

5-(2,4-Difluorophenoxy)-2-[3-methoxy-4-(2-pyrrolidin-1-yl-ethoxy)-phenyl]-isoindole-1,3-dione Using the method of Example A15 but utilising 2,4-difluorophenol [Aldrich] in place of 4-chlorophenol to give the title compound as the trifluoroacetate salt.

EXAMPLE A35

5-(4-Fluoro-2-methoxyphenoxy)-2-[3-methoxy-4-(2-pyrrolidin-1-yl-ethoxy)-phenyl]-isoindole-1,3-dione Using the method of Example A15 but utilising 4-fluoro-2-methoxyphenol [Aldrich] in place of 4-chlorophenol to give the title compound as the trifluoroacetate salt.

EXAMPLE A36

5-(2-Methoxyphenoxy)-2-[3-methoxy-4-(2-pyrrolidin-1-yl-ethoxy)-phenyl]-isoindole-1,3-dione Using the method of Example A15 but utilising 2-methoxyphenol [Aldrich] in place of 4-chlorophenol to give the title compound as the trifluoroacetate salt.

EXAMPLE A37

5-(Cyclohex-2-enyloxy)-2-[3-methoxy-4-(2-pyrrolidin-1-ylethoxy)phenyl]isoindol-1,3-dione Using the procedure of Example A39 but utilising racemic 2-cyclohexenol [Aldrich] in place of 3-methyl-2-butenol to give first 4-(cyclohex-2-enyloxy)-phthalic acid dimethyl ester;
$^1$H NMR (CDCl$_3$): δ 1.60–2.20 (m, 6H), 3.86 (s, 3H), 3.90 (s, 3H), 4.85–4.90 (m, 1H), 5.81–5.85 (m, 1H), 5.98–6:02 (m, 1H), 6.99 (d, J 8.8, 1H), 7.07 (s, 1H), 7.79 (d, J 8.8, 1H).

This was progressed in the same manner as 4-(3-methylbut-2-enyloxy)phthalic acid dimethyl ester in the same example to give the title compound as the hydrochloride salt, a racemate.

EXAMPLE A38

2-[3-Methoxy-4-(2-pyrrolidin-1-ylethoxy)phenyl]-5-(pent-2-enyloxy)isoindol-1,3-dione Using the procedure of Example A39 but utilising a 2.7:1 mixture of Z and E-pent-2-enol [Aldrich] in place of 3-methyl-2-butenol to give the title compound as a 2.7:1 mixture of Z and E isomers as their hydrochloride salts

EXAMPLE A39

2-[3-Methoxy-4-(2-pyrrolidin-1-ylethoxy)phenyl]-5-(3-methylbut-2-enyloxy)isoindol-1,3-dione 3-Methyl-2-butenol [Aldrich] was used in place of allyl alcohol in the procedure described in *Angew. Chem.*, 1992, 104, 198–200, to prepare 4-allyloxyphthalic acid dimethyl ester. This gave 4-(3-methylbut-2-enyloxy)phthalic acid dimethyl ester;
$^1$H NMR (CDCl$_3$): δ 1.74 (s, 3H), 1.80 (s, 3H), 3.86 (s, 3H), 3.91 (s, 3H), 4.56 (d, J 6.7, 2H), 5.44–5.48 (m, 1H), 6.98 (d, J 8.6, 1H), 7.07 (s, 1H), 7.79 (d, J 8.6, 1H).

This material was treated by the same procedure used in *Angew. Chem.*, 1992, 104, 198–200, to prepare 4-allyloxyphthalic acid from 4-allyloxyphthalic acid dimethyl ester, and afforded 4-(3-methylbut-2-enyloxy)phthalic acid;
$^1$H NMR (CD$_3$OD): δ 1.76 (s, 3H), 1.79 (s, 3H), 4.62 (d, J 6.8, 2H), 5.44–5.47 (m, 1H), 7.05 (d, J 8.8, 1H), 7.09 (s, 1H), 7.81 (d, J 8.8, 1H).

A mixture of this acid (67 mg, 0.27 mmol), 3-methoxy-4-(2-pyrrolidin-1-yl-ethoxy)-phenylamine [Example A4]

(67 mg, 0.28 mmol) and N-cyclohexylcarbodiimide resin (1.69 mol. eq./g, 0.46 g, 0.78 mmol) was stirred in a 50:50 mixture of DMF and dichloromethane (1.5 ml) at room temperature under argon for 16 h. The mixture was filtered through filter-aid and the resin washed several times with dichloromethane. The filtrate was evaporated and the crude residue purified by flash chromatography on silica gel eluting with methanol in dichloromethane to yield the title compound as a brown oil;

$^1$H NMR (CDCl$_3$): δ 1.78 (s, 3H), 1.82–1.87 (m, 7H), 2.62–2.80 (m, 4H), 3.01 (t, J 6.0, 2H), 3.86 (s, 3H), 4.22 (t, J 6.4, 2H), 4.66 (d, J 6.8, 2H), 5.47–5.51 (m, 1H), 6.92–7.01 (m, 3H), 7.21 (d, J 8.4, 1H), 7.40 (s, 1H), 7.82 (d, J 8.4, 1H), which was converted to the hydrochloride salt by treatment with ethereal hydrogen chloride (1M).

EXAMPLE A40

2-[3-Methoxy-4-(2-pyrrolidin-1-ylethoxy)phenyl]-5-(2-methylallyloxy)isoindol-1,3-dione Using the procedure of Example A39 but utilising 2-methyl-propenol [Aldrich] in place of 3-methyl-2-butenol to give the title compound as the hydrochloride salt.

EXAMPLE A41

5-(Cyclopent-2-enyloxy)-2-[3-methoxy-4-(2-pyrrolidin-1-yl-ethoxy)-phenyl]isoindole-1,3-dione Using the procedure of Example A39 but utilising racemic 2-cyclopentenol [Wiley] in place of 3-methyl-2-butenol to give the title compound as the hydrochloride salt, a racemate.

EXAMPLE A42

5-Cyclohexyloxy-2-[3-methoxy-4-(2-pyrrolidin-1-ylethoxy)phenyl]isoindol-1,3-dione 4-(Cyclohex-2-enyloxy)-phthalic acid dimethyl ester [Example A37] (67 mg, 0.23 mmol) was hydrogenated under an atmosphere of hydrogen at room temperature and pressure with 10% wet Pd/C (ca. 200 mg) in THF (5 mL) for 24 h. The catalyst was removed by filtration and the solvent was evaporated under vacuum. The crude material was purified by flash chromatography on silica gel eluting with 0–20% MeOH in DCM to yield 4-cyclohexyloxy-phthalic acid dimethyl ester as an oil. m/z (APCI+) 293 (15%, [M+H]$^+$), 179 (100), 261 (65).

This was used in the procedure of Example A39 in place of 4-(3-methylbut-2-enyloxy)phthalic acid dimethyl ester to give the title compound;

$^1$H NMR (CDCl$_3$): δ 1.30–2.03 (m, 14H), 2.68–2.80 (m, 4H), 3.01 (t, 2H), 3.86 (s, 3H), 4.22 (t, 2H), 4.40–4.46 (m, 1H), 6.92–7.00 (m, 3H), 7.19 (d, 1H), 7.38 (s, 1H), 7.81 (d, 1H); m/z (APCI–) 463 (20%, [M–H]$^-$), 381 (100%).

EXAMPLE A43

5-(Cyclopentyloxy)-2-[3-methoxy-4-(2-pyrrolidin-1-yl-ethoxy)-phenyl]-isoindole-1,3-dione Using the procedure of Example A42 but utilising racemic 4-(cyclopent-2-enyloxy)-phthalic acid dimethyl ester [Example A41] in place of 4-(cyclohex-2-enyloxy)-phthalic acid dimethyl ester to give the title compound as the hydrochloride salt, a racemate

EXAMPLES B1, B2

2-[4-(2-Diisopropylamino-ethoxy)-3-methoxy-phenyl]-5-phenyl-2,3-dihydro-isoindol-1-one 2-[4-(2-Diisopropylamino-ethoxy)-3-methoxy-phenyl]-6-phenyl-2,3-dihydro-isoindol-1-one A solution of 5-bromo-2-[4-(2-diisopropylamino-ethoxy)-3-methoxy-phenyl]-isoindole-1,3-dione [Example A1] (66 mg, 0.14 mmol) was dissolved in THF (ml) and treated with sodium borohydride (5.2 mg, 0.14 mmol). After stirring for 2 hours, the mixture was treated with isopropanol, stirred for a further 1 h then treated with acetic acid (2 drops) and stirred for 16 h at RT. The solvent was removed and the residue purified by flash chromatography to give an approximately 1:1 mixture of the 5- and 6-bromo substituted isomers of 2-[4-(2-diisopropylamino-ethoxy)-3-methoxy-phenyl]-3-hydroxy-2,3-dihydro-isoindol-1-one (37 mg). This material was dissolved in dichloromethane (2 ml) and treated with triethylsilane (1 ml) and trifluoroacetic acid (0.5 ml). The mixture was stirred at RT for 16 hours, the solvents were removed in vacuo and the residue purified by flash chromatography on silica gel (eluting with methanol-dichloromethane-aq. ammonia) to obtain 2-[4-(2-diisopropylamino-ethoxy)-3-methoxy-phenyl]-2,3-dihydro-isoindol-1-one as an approximately 1:1 mixture of 5- and 6-bromo isomers (33 mg). A solution of this material in benzene (5 ml) was treated with aqueous sodium carbonate (2M, 1 ml), ethanol (1 ml), phenylboronic acid (9 mg, 0.07 mmol) and tetrakis(triphenylphosphine)palladium[0] (10 mg) and the mixture heated to reflux for 16 h. The less dense phase was decanted, filtered through filter-aid (washing with dichloromethane), the filtrate evaporated and purified by flash chromatography on silica gel (eluting with dichloromethane-methanol-aq. ammonia) and reverse phase preparative chromatography (aq. MeCN, TFA) to give the title compounds as an approximately 1:1 mixture of isomers as their TFA salts;

$^1$H NMR (CDCl$_3$): δ 1.5 (bd, 12H), 3.47 (d, 2H), 3.82 (m, 2H), 3.93 (s. 3H), 4.5 (t, 2H), 4.88, 4.89 (2s, 2H), 6.94–7.05 (2H, m), 7.25–7.75 (7H, m), 7.84 (0.5H, dd), 7.96 (0.5H, dd), 8.08–8.17 (1H, m), 12.5 (1H, bs) (m/z AP+) 459.

EXAMPLE B3

2-[3-Methoxy-4-(2-pyrrolidin-1-yl-ethoxy)-phenyl]-S-phenoxy-2,3-dihydro-isoindol-1-one Utilising the procedure outlined in Example B1/B2 but with 2-[3-methoxy-4-(2-pyrrolidin-1-yl-ethoxy)-phenyl]-5-phenoxy-isoindole-1,3-dione [Example A4] in place of 5-bromo-2-[4-(2-diisopropylamino-ethoxy)-3-methoxy-phenyl]-isoindole-1,3-dione gave the title compound in place of 5/6-bromo-2-[4-(2-diisopropylamino-ethoxy)-3-methoxy-phenyl]-2,3-dihydro-isoindol-1-one, but as the single isomer, as a TFA salt:

$^1$H NMR (CDCl$_3$): δ 2.1 (bd, 4H), 3.1 (2H, bm), 3.5 (2H, bs), 3.89 (s, 3H), 3.9 (bs, 2H), 4.43 (2H, bs), 4.7 (s, 2H), 6.90–7.44 (m, 9H), 7.93 (d, 1H), 7.94 (d, 1H), 12.5 (bs 1H).

EXAMPLE C1

3-[3-Methoxy-4-(2-pyrrolidin-1-yl-ethoxy)-phenyl]-7-phenoxy-3H-benzol[d][1,2,3]triazin-4-one A solution of 2,4-dinitrobenzoic acid [Aldrich] (1.06 g, 5 mmol) in dichloromethane (20 ml) was treated with oxalyl chloride (2 ml) and 1 drop DMF. Vigorous evolution of gas occurred which ceased after 1 hour. The solution was evaporated to the yellow acid chloride. A solution of phenol (1.5 g, 15.5 mmol) in DMF (20 ml) was introduced into a second flask charged with sodium hydride (480 mg, 60% oil dispersion, 12 mmol). When all the hydride had dissolved this solution was treated with the acid chloride, portionwise over five minutes. The solution was then heated to 60° C. for 12 h, cooled, the solvents removed by evaporation in vacuo, and the residue treated with a solution of 40% sodium hydroxide (50 ml) and ethanol (50 ml). The mixture was stirred at RT for 12 hours then acidified to pH 2 with (2M aq HCl) and extracted into ethyl acetate (3×100 ml). The combined organic phase was washed with saturated brine (50 ml), dried ($MgSO_4$), filtered, and evaporated to a yellow solid. This was purified by flash chromatography (ethyl acetate-hexane) to give 2-nitro-4-phenoxy-benzoic acid (894 mg, 69%);

$^1$H NMR ($CDCl_3$): δ 4.8 (1H, bs), 7.10 (1H, dd), 7.16 (1H, dd), 7.21 (1H, d), 7.26–7.31 (2H, m), 7.46 (2H, dd), 7.94, (1H, d).

This acid (445 mg, 1.72 mmol) was dissolved in dichloromethane (10 ml) and treated with oxalyl chloride (2 ml) and 1 drop of DMF. Vigorous evolution of gas occurred which ceased after 1 hour. The solution was evaporated to the yellow acid chloride. This was dissolved in dichloromethane (10 ml) and treated with 3-methoxy-4-(2-pyrrolidin-1-yl-ethoxy)-phenylamine [Example A4] and diethylisopropylamine polystyrene resin beads (3.49 mol. eq./g, 0.6 g). The mixture was shaken for 12 hours then filtered, evaporated and purified by flash chromatography on silica gel (eluting with ammonia-methanol-dichloromethane) to give N-[3-methoxy-4-(2-pyrrolidin-1-yl-ethoxy)-phenyl]-2-nitro-4-phenoxy-benzamide as a yellow foam (600 mg, 73%);

$^1$H NMR ($CDCl_3$): δ 1.81 (4H, m), 2.64 (4H, m), 2.94 (2H, t), 3.84 (3H, s), 4.14 (2H, t), 6.84 (1H, d), 6.93 (1H, dd), 7.08 (2H, d), 7.22–7.47 (5H, m), 7.56–7.60 (2H, m), 7.80 (1H, bs); m/z [AP+] 478 (M+H$^+$, 100%).

This amine (400 mg, 0.83 mmol) was dissolved in ethanol (40 ml) and treated with 10% palladium on carbon (250 mg), then the mixture was hydrogenated at atmospheric pressure for 18 hours. The mixture was filtered and the solvent removed in vacuo to give 2-amino-N-[3-methoxy-4-(2-pyrrolidin-1-yl-ethoxy)-phenyl]-4-phenoxy-benzamide as a cream solid (380 mg, 100%);

$^1$H NMR ($CDCl_3$): δ 1.99 (4H, bs), 3.14 (4H, bs), 3.24 (2H, t), 3.82 (3H, s), 4.30 (2H, t), 5.58 (2H, bs), 6.22 (1H, d), 6.30 (11H, dd), 6.81 (1H, d), 6.98 (1H, dd), 7.04 (2H, d), 7.15 (1H, t), 7.34–7.42 (3H, m), 7.57 (1H, d), 8.21 (1H, bs); m/z [AP+] 459 (M+H$^+$, 100%).

This amine (58 mg, 0.13 mmol) was dissolved in dichloromethane (5 ml) and acidified with trifluoroacetic acid (200 ul) then treated with butyl nitrite [Aldrich] (0.1 ml); a brown colour immediately appeared. After 1 minute, the mixture was treated with 1,8-diazabicyclo[5.4.0]undec-7-ene (DBU) [Aldrich] (0.5 ml). The colour immediately faded. The solvent was removed and the residue purified by flash chromatography using silica gel (eluting with dichloromethane-methanol-ammonia) to give the title compound;

$^1$H NMR ($CDCl_3$): δ 1.83 (4H, m), 2.69 (4H, m), 3.01 (2H, t), 3.90 (3H, m), 4.24 (2H, t), 7.03 (1H, d), 7.14–7.18 (4H, m), 7.30 (1H, t), 7.50–7.54 (4H, m), 8.39 (1H, d) which was crystallized from ether-HCl as the hydrochloride salt, a pale yellow solid

EXAMPLE $C_2$

3-[3-Methoxy-4-(2-pyrrolidin-1-yl-ethoxy)-phenyl]-7-phenoxy-3H-quinazolin-4-one 2-Amino-N-[3-methoxy-4-(2-pyrrolidin-1-yl-ethoxy)-phenyl]-4-phenoxy-benzamide [Example C1] (50 mg, 0.11 mmol) was dissolved in 1,2-dichloroethane (5 ml) and treated with triethylorthoformate [Aldrich] (2 ml) then heated to reflux for 12 h. The mixture was cooled and DBU (0.1 ml) introduced. The solvent was evaporated then the residue purified by flash chromatography on silica gel (eluting with ammonia-methanol-dichloromethane) to obtain the title compound;

$^1$H NMR ($CDCl_3$): δ 1.86 (4H, m), 2.69 (4H, m), 3.02 (2H, t), 3.88 (3H, t), 4.24 (2H, t), 6.89–6.93 (2H, m), 7.01 (1H, d), 7.12–7.26 (5H, m), 7.43 (2H, t), 8.07 (1H, s), 8.31 (1H, dd); which was crystallized from ether-HCl as the hydrochloride salt, a white solid.

EXAMPLE C3

3-[3-Methoxy-4-(2-pyrrolidin-1-yl-ethoxy)-phenyl]-7-phenoxy-1H-quinazoline 2,4-dione 2-Amino-N-[3-methoxy-4-(2-pyrrolidin-1-yl-ethoxy)-phenyl]-4-phenoxy-benzamide [Example C1] (62 mg, 0.14 mmol) was dissolved in dichloromethane (5 ml) and treated with carbonyl diimidazole (50 mg, 0.31 mmol) and DBU (0.1 ml). The mixture was stirred for 4 h at RT then the solvent removed and the residue purified by flash chromatography on silica gel (eluting with ammonia-methanol-dichloromethane) to obtain the title compound;

$^1$H NMR ($CDCl_3$): δ 1.79 (4H, m), 2.64 (4H, m), 2.97 (2H, t), 3.82 (3H, s), 4.20 (2H, t), 6.46 (1H, d), 6.76–6.83 (3H, m), 6.98 (1H, d), 7.09 (2H, d), 7.23–7.27 (1H, m), 7.40–7.44 (2H, m), 8.08 (1H, d), 8.8 (1H, bs);

which was crystallized from ether-HCl as the hydrochloride salt, a white solid.

EXAMPLE C4

3-[3-Methoxy-4-(2-pyrrolidin-1-yl-ethoxy)-phenyl]-2-methyl-7-phenoxy-3H-quinazolin-4-one 2-Amino-N-[3-methoxy-4-(2-pyrrolidin-1-yl-ethoxy)-phenyl]-4-phenoxy-benzamide [Example C1] (50 mg, 0.11 mmol) was dissolved in 1,2-dichloroethane (5 ml) and treated with triethylorthoacetate [Aldrich] (2 ml) then heated to 100° C. for 12 h. The mixture was cooled and DBU (0.1 ml) introduced. The solvent was evaporated then the residue purified by flash chromatography on silica gel (eluting with aq. ammonia-methanol-dichloromethane) to obtain the title compound as a white solid;

$^1$H NMR ($CDCl_3$): δ 1.82 (4H, m), 2.23 (3H, s), 2.67 (4H, m), 3.00 (2H, t); 3.86 (3H, s), 4.22 (2H, t), 6.72 (1H, d), 6.77 (1H, dd), 7.00–7.04 (2H, m), 7.12–7.22 (3H, m), 7.26 (1H, t), 7.42 (2H, t), 8.22 (1H, d).

EXAMPLE C5

3-[3-Methoxy-4-(2-pyrrolidin-1-yl-ethoxy)-phenyl]-7-phenyl-3H-benzo[d][1,2,3]triazin-4-one 3-Nitrobiphenyl (3.0 g, 15 mmol), was dissolved in DMF (7.5 ml) and dry chloroform (16.5 mmol). This mixture was added dropwise to a stirred precooled mixture of potassium tert-butoxide (7.2 mg, 60 mmol) in DMF (20 ml) and THF (25 ml), at such a rate that the temperature was maintained between −69 and −73° C. When the addition was complete, the mixture was stirred for a further 1 minute then treated with acetic acid (1.5 ml) in methanol (5 ml) and allowed to warm to room temperature. The mixture was treated with saturated aqueous sodium bicarbonate (50 ml) and extracted with dichloromethane (3×5 ml), the combined organic phase dried (MgSO$_4$), filtered and evaporated, then the residue purified by flash chromatography (ether-hexane). This gave a yellow material which consisted of between 30 and 50% of dichloromethylsubstituted 3-nitrobiphenyl and starting material. The mixture was dissolved in acetonitrile (10 ml) and treated with a solution of silver trifluoromethanesulphonate (15 mmol, 3.84 g) in water (5 ml). The mixture was heated to reflux for 16 h in the dark then cooled, the mixture concentrated in vacuo, filtered and the filtrate extracted with ether (3×50 ml). The combined organic phase was evaporated and purified by flash chromatography to give 3-nitro-biphenyl-4-carbaldehyde;

$^1$H NMR (CDCl$_3$): δ 7.51–7.58 (3H, m), 7.29 (3H, s), 7.51–7.58 (3H, m), 7.69 (2H, dd), 8.03, 8.08 (2H, 2×d), 8.34 (1H, d), 10.49 (1H, s).

This aldehyde (454 mg, 2.0 mmol) was dissolved in acetic acid (10 ml) and treated with sodium perborate tetrahydrate (385 mg, 2.5 mmol), the mixture was heated to 50° C. for 48 h then cooled, concentrated to a paste and washed with water (2×50 ml). The residue was dried in a desiccator to afford 3-nitrobiphenyl-4-carboxylic acid as a white solid (420 mg, 87%);

$^1$H NMR (CDCl$_3$): δ 5.5 (1H, bs), 7.48–7.56 (4H, m), 7.30 (1H, bs), 7.50–7.77 (3H, m).

This acid (417 g, 1.72 mmol) was dissolved in dichloromethane (10 ml) and treated with oxalyl chloride (2 ml) and 1 drop of DMF. Vigorous evolution of gas occurred which ceased after 1 hour. The solution was evaporated to the yellow acid chloride. This was dissolved in dichloromethene (10 ml) and treated with 3-methoxy-4-(2-pyrrolidin-1-yl-ethoxy)-phenylamine [Example C1] (472 mg, 2 mmol) and diethylisopropylamine polystyrene resin beads (1.0 g, 3.6 mmol equiv). The mixture was shaken for 12 hours then filtered, evaporated and purified by flash chromatography on silica gel (eluting with ammonia-methanol-dichloromethane) to give N-[3-methoxy-4-(2-pyrrolidin-1-yl-ethoxy)-phenyl]-2-nitro-4-phenyl-benzamide as a yellow foam (563 mg, 71%);

$^1$H NMR (CDCl$_3$): δ 1.78 (4H, bs), 2.61 (4H, bs), 2.91 (2H, t), 3.79 (3H, s), 4.10 (2H, t), 6.80 (1H, d), 6.98 (1H, dd), 7.32 (1H, d), 7.42–7.50 (3H, m), 7.57 (2H, d), 7.66 (1H, d), 7.83 (1H, dd), 8.20 (2H, dd). m/z [AP+] 462 (M+H$^+$, 100%).

This amine (560 mg, 1.3 mmol) was dissolved in ethanol (20 ml) and treated with 10% palladium on carbon (100 mg) then the mixture hydrogenated at atmospheric pressure for six hours. The mixture was filtered and the solvent removed in vacuo to give 2-amino-N-[3-methoxy-4-(2-pyrrolidin-1-yl-ethoxy)-phenyl]-4-phenyl-benzamide as a cream solid (518 mg, 99%);

$^1$H NMR (CDCl$_3$): δ 1.82 (4H, m), 2.68 (4H, m), 2.96 (2H, t), 3.86 (3H, s), 4.16 (2H, t), 5.6 (2H, bs), 6.86–6.97 (4H, m), 7.35–7.58 (7H, m), 7.89 (1H, bs). m/z [AP+] 431(M+H$^+$ 100%).

This amine was treated in the manner of 2-amino-N-[3-methoxy-4-(2-pyrrolidin-1-yl-ethoxy)-phenyl]-4-phenoxy-benzamide in Example C1 to give the title compound;

$^1$H NMR (CDCl$_3$): δ 1.86 (4H, m), 2.73 (4H, m), 3.05 (2H, t), 3.91 (3H, t), 4.29 (2H, t), 7.06 (1H, d), 7.18–7.24 (2H, m), 7.47–7.57 (3H, m), 7.76 (2H, d), 8.06 (1H, d), 8.42 (1H, d), 8.49 (1H, d).

which crystallised from Et$_2$O/HCl as a pale yellow solid.

EXAMPLE C6

3-[3-Methoxy-4-(2-pyrrolidin-1-yl-ethoxy)-phenyl]-7-phenyl-3H-quinazolin-4-one Using 2-amino-N-[3-methoxy-4-(2-pyrrolidin-1-yl-ethoxy)-phenyl]-4-phenyl-benzamide [Example C5] in the manner of 2-amino-N-[3-methoxy-4-(2-pyrrolidin-1-yl-ethoxy)-phenyl]-4-phenoxy-benzamide in Example C2, gave the title compound as a cream solid;

$^1$H NMR (CDCl$_3$): δ 1.83 (4H, m), 2.69 (4H, m), 3.01 (2H, t), 3.90 (3H, t), 4.24 (2H, t), 6.92–6.96 (2H, m), 7.03 (1H, d), 7.43–7.53 (3H, m), 7.72 (2H, d), 7.79 (1H, dd), 7.98 (1H, d), 8.15 (1H, s), 8.42 (1H, d).

EXAMPLE C7

3-[3-Methoxy-4-(2-pyrrolidin-1-yl-ethoxy)-phenyl]-7-phenyl-1N-quinazoline-2,4-dione Using 2-Amino-N-[3-methoxy-4-(2-pyrrolidin-1-yl-ethoxy)-phenyl]-4-phenyl-benzamide [Example C5] in the manner of 2-amino-N-[3-methoxy-4-(2-pyrrolidin-1-yl-ethoxy)-phenyl]-4-phenoxy-benzamide in Example C3, gave the title compound;

$^1$H NMR (CDCl$_3$): δ 1.82 (4H, m), 2.67 (4H, m), 2.99 (2H, t), 3.83 (3H, s), 4.21 (2H, t), 6.81 (1H, d), 6.85 (1H, dd), 7.00 (1H, d), 7.23 (1H, d), 7.45–7.52 (4H, m), 7.62 (2H, d), 7.66 (1H, s), 8.21 (1H, d);

which crystallised from diethyl ether/HCl as a cream solid.

EXAMPLE C8

3-[3-Methoxy-4-(2-pyrrolidin-1-yl-ethoxy)-phenyl]-2-methyl-7-phenoxy-3H-quinazolin-4-one Using 2-amino-N-[3-methoxy-4-(2-pyrrolidin-1-yl-ethoxy)-phenyl]-4-phenyl-benzamide [Example C5] in the manner of 2-amino-N-[3-methoxy-4-(2-pyrrolidin-1-yl-ethoxy)-phenyl]-4-phenoxy-benzamide in Example C4, gave the title compound;

$^1$H NMR (CDCl$_3$): δ 1.85 (4H, m), 2.31 (3H, s), 2.69 (4H, m), 3.02 (2H, t), 3.87 (3H, t), 4.24 (2H, t), 6.76 (1H, d), 6.83 (1H, dd), 7.04 (1H, d), 7.41–7.52 (3H, m), 7.70–7.91 (3H, m), 7.91 (1H, d), 8.32 (1H, d).

EXAMPLE C9

7-Allyloxy-3-[3-methoxy-4-(2-pyrrolidin-1-ylethoxy)phenyl]-3H-quinazolin-4-one hydrochloride 4-allyloxy-2-nitro-benzoic acid allyl ester [J. Org. Chem. 1987, 52(18), 4086] (0.21 g, 0.8 mmol) was dissolved in ethanol (5 ml), and 40% sodium hydroxide added (5 ml). The mixture was stirred for 16 h then acidified to pH 2 with 2M hydrochloric acid. The mixture was extracted with ethyl acetate (3×25 ml) and the combined organic phases washed with brine (75 ml), dried (MgSO$_4$) and concentrated to yield 4-allyloxy-2-nitrobenzoic acid as brown solid (0.16 g);

$^1$H-NMR (DMSO) δ 4.72–4.74 (m, 2H), 5.29–5.45 (dd, 2H), 5.99–6.07 (m, 1H), 7.28–7.31 (dd, 1H), 7.49–7.50 (d, 1H), 7.82–7.87 (d, 1H) 13.45 (bs, 1H).

This acid (0.16 g, 0.72 mmol) was dissolved in dichloromethane (1 ml) and oxalyl chloride (0.2 ml) added, followed by 1 drop of DMF. The mixture was stirred under argon for 1 hr and concentrated to yield 4-allyloxy-2-nitrobenzoyl chloride, an orange solid (0.173 g). This was redissolved in dichloromethane (5 ml) and added dropwise to a stirred solution of 3-methoxy-4-(2-pyrrolidin-1-yl-ethoxy)-phenylamine [Example C1] (154 mg, 0.66 mmol) and triethylamine (72.8 mg, 0.72 mmol) in 5 ml dichloromethane. The mixture was stirred for 90 minutes, then the solution washed with saturated sodium hydrogen carbonate (25 ml), and brine (25 ml). The residue was dried (MgSO$_4$) and concentrated to yield 4-allyloxy-N-[3-methoxy-4-(2-pyrrolidin-1-ylethoxy)phenyl]-2-nitro-benzamide a brown solid (191.5 mg);

$^1$H-NMR (CDCl$_3$) δ 1.93 (bs, 4H), 3.04 (bm, 4H), 2.80–2.81 (bm, 2H), 3.74 (s, 3H), 4.21 (bm, 2H), 4.61–4.63 (bd, 2H), 5.30–5.47 (dd, 2H), 5.98–6.08(m, 1H), 6.75–6.77 (d, 1H), 6.96–6.99 (dm, 1H), 7.14–7.17 (dm, 1H), 7.49–7.50 (d, 2H), 7.57–7.59 (d, 1H), 8.59 (s, 1H).

A solution of this material (191.5 mg, 0.43 mmol) in methanol was added dropwise to a stirred suspension of iron powder (72.6 mg, 1.3 mmol) and ammonium chloride (115.8 mg, 2.17 mmol) in water (5 ml). The mixture was heated to 80° C. for 90 mins, then hot filtered through celite. The filter cake was washed with dichloromethane (10 ml) and water (10 ml). The organic phase was separated and the aqueous layer basified with saturated sodium hydrogen carbonate. The aqueous layer was extracted with dichloromethane (3×10 ml) and the combined organic layers washed with brine (10 ml), then dried (MgSO$_4$) and concentrated to yield 4-allyloxy-2-amino-N-[3-methoxy-4-(2-pyrrolidin-1-ylethoxy)phenyl]-benzamide as a yellow gum;

$^1$H-NMR (DMSO) δ1.76–1.82 (bm, 4H), 2.62–2.64 (bm, 4H), 2.92–2.85 (t, 2H), 3.85 (s, 3H), 4.12–4.16 (t, 2H), 4.51–4.53 (m, 2H), 5.28–5.42 (m, 2H), 5.63 (bs, 2H), 5.99–6.06 (m, 1H), 6.18–6.19 (d, 1H), 6.26–6.29 (dd, 2H), 6.85–6.91 (m, 3H), 7.29–7.38 (d, 1H), 7.62 (s, 1H).

This material was treated in the same manner as 2-amino-N-[3-methoxy-4-(2-pyrrolidin-1-yl-ethoxy)-phenyl]-4-phenoxy-benzamide [Example C1] in the method of Example C2 to afford 7-allyloxy-3-[3-methoxy-4-(2-pyrrolidin-1-ylethoxy)phenyl]-3H-quinazolin-4-one which was crystallised from ether-HCl to give the title compound as a yellow solid (21.5 mg);

$^1$H-NMR (CDCl$_3$) δ 2.11–2.25 (bd, 4H), 3.06 (bs, 2H), 3.54–3.57 (bd, 2H), 3.88 (bs, 5H), 4.62 (bs, 2H), 4.69–4.72 (dm, 2H), 5.35–5.53 (dd, 2H), 6.03–6.10 (m, 1H), 6.96 (bs, 2H), 7.07–7.10 (d, 1H), 7.17–7.21 (dd, 1H), 7.31–7.32 (d, 1H), 8.23–8.27 (d, 1H), 8.36 (s, 1H), 12.85 (bs, 1H).

EXAMPLE D1

3-[3-Methoxy-4-(2-pyrrolidin-1-yl-ethoxy)phenyl]-6-phenoxy-3H-benzo[d][1,2,3]triazin-4-one 5-Chloro-2-nitrobenzoic acid [Aldrich] (600 mg, 3 mmol) was suspended in dichloromethane (5 ml) and treated with oxalyl chloride (2 ml) and DMF (1 drop). On stirring, an immediate effervescence occurred which ceased after 1 hour. The solvent was removed in vacuo and the residue dissolved in dichloromethane (10 ml) and treated successively with DIEA resin (3.1 mmol/g, 1.95 g) and 3-methoxy-4-(2-pyrrolidin-1-yl-ethoxy)-phenylamine (650 mg, 3 mmol). The mixture was stirred at RT for 16 hours then filtered, evaporated, and the residue purified by flash chromatography (methanol-dichloromethane-aqueous ammonia) to afford 5-chloro-N-[3-methoxy-4-(2-pyrrolidin-1-yl-ethoxy)-phenyl]-2-nitro-benzamide as a yellow foam;

$^1$H NMR (CDCl$_3$): δ 1.86 (4H, m), 2.68 (4H, m), 2.98 (2H, t), 3.87 (3H, s), 4.16 (2H, t), 6.87 (1H, d), 6.94 (1H, dd), 7.34 (1H, d), 7.56–7.64 (3H, m), 8.09 (1H, d); m/z [AP+] 420 (100%, (M+H$^+$), 422.

A solution of this material (210 mg, 0.5 mmol) in DMF (2 ml) was treated with phenol (94 mg, 1 mmol) and sodium hydride (60% oil dispersion, 36 mg, 0.9 mmol) then the mixture heated to 60° C. for 48 h. The solution was cooled, evaporated and the residue suspended in dichloromethane and filtered. The filtrate was evaporated and purified by flash chromatography on silica gel (eluting with methanol-dichloromethane-aqueous ammonia) to afford N-[3-methoxy-4-(2-pyrrolidin-1-yl-ethoxy)-phenyl]-2-nitro-5-phenoxy-benzamide (200 mg, 84%) as a yellow wax;

$^1$H NMR (CDCl$_3$): δ 1.80 (4H, m), 2.62 (4H, m), 2.92 (2H, t), 3.82 (3H, s), 4.12 (2H, t), 6.83 (1H, d), 6.93 (1H, dd), 7.03–7.11 (4H, m), 7.26–7.41 (2H, m), 7.43 (2H, m), 7.77 (1H, m), 8.11 (1H, d) m/z [AP+] 420 (100% M+H$^+$).

A solution of this amine (100 mg, 0.24 mmol) in ethanol (10 ml) was treated with 10% palladium on carbon (50% wet, 100 mg), and hydrogenated at RT for 12 hours. The mixture was filtered, and the solvent removed in vacuo to give 2-amino-N-[3-methoxy-4-(2-pyrrolidin-1-yl-ethoxy)-phenyl]-5-phenoxy-benzamide as a white waxy solid, a portion of which was crystallised from Et$_2$O/HCl to give the hydrochloride salt $^1$H NMR (CDCl$_3$): δ 1.99–2.11 (6H, bm), 2.97 (2H, bs), 3.39 (2H, bs), 3.77 (3H, s), 4.38 (2H, bs), 5.5 (2H, bs), 6.66 (1H, d); 6.78–6.98 (6H, m), 7.20–7.24 (1H, m), 7.36 (1H, s), 8.06 (1H, brs), 12.5 (1H, brs) m/z [AP+] 448 (100%, M+H$^+$).

A solution of the free base of this amine (58 mg, 0.13 mmol) in dichloromethane (2 ml) was acidified with 5 drops of TFA then treated with butyl nitrite (100 ul). A deep orange colour formed immediately. After 1 minute, DBU was introduced dropwise until basic. The solvent was removed in vacuo and the residue purified by flash chromatography on silica gel (eluting with methanol-dichloromethane-aqueous ammonia) to give the title compound which crystallised as a pale yellow HCl salt on treatment with 1M HCl in ether;

$^1$H NMR (CDCl$_3$): δ 2.11, 2.25 (4H, 2xm), 3.07 (2H, m), 3.53 (2H, m), 3.88 (3H, s), 3.92 (2H, m), 4.61 (2H, t), 7.08 (1H, d), 7.12 (2H, d), 7.16–7.27 (2H, m), 7.45 (2H, t), 7.64 (1H, dd), 7.76 (1H, d), 8.20 (1H, d), 12.9 (1H, bs).

EXAMPLE D2

3-[3-Methoxy-4-(2-pyrrolidin-1-yl-ethoxy)-phenyl]-6-phenoxy-3H-quinazolin-4-one

A solution of 2-amino-N-[3-methoxy-4-(2-pyrrolidin-1-yl-ethoxy)-phenyl]-5-phenoxy-benzamide [Example D1] (25 mg, 0.055 mmol) in 1,2-dichloroethane (1 ml) was treated with triethylorthoformate (2 ml) and the mixture heated to 80° C. for 16 hours. The mixture was cooled, 1 drop of DBU added and the mixture evaporated. The residue was subjected to flash chromatography on silica gel eluting with (methanol-dichloromethane-aqueous ammonia) to give the title compound;

$^1$H NMR (CDCl$_3$): δ 1.83 (4H, m), 2.67 (4H, m), 2.99 (2H, t), 3.88 (3H, s), 4.22 (2H, t), 6.89–6.92 (2H, m), 7.01 (1H, d), 7.08 (2H, d), 7.17 (1H, t), 7.38 (2H, t), 7.53 (1H, dd), 7.76 (1H, d), 7.84 (1H, d), 8.05 (1H, s); which crystallised as a pale yellow HCl salt on treatment with 1M HCl in ether.

EXAMPLE D3

3-[Methoxy-4-(2-pyrrolidin-1-yl-ethoxy)phenyl]-6phenoxy-1H-quinazoline-2,4-dione A solution of 2-amino-N-[3-methoxy-4-(2-pyrrolidin-1-yl-ethoxy)-phenyl]-5-phenoxy-benzamide [Example D1] (25 mg, 0.055 mmol) in dichloromethane (1 ml) was treated with carbonyl diimidazole (16 mg, 0.1 mmol), and DBU (1 drop). The mixture was stirred at RT for 4 hours then evaporated and the residue purified by flash chromatography on silica gel (eluting with methanol-dichloromethane-aqueous ammonia) to give the title compound;

$^1$H NMR (CDCl$_3$): δ 1.84 (4H, m), 2.0 (1H, brs), 2.74 (4H, m), 3.03 (2H, t), 3.82 (3H, s), 4.23 (2H, t), 6.77–6.84 (2H, m), 6.98–7.03 (4H, m), 7.12 (1H, t), 7.31–7.36 (3H, m), 7.71 (1H, d); which crystallised as a white HCl salt on treatment with 1M HCl in ether.

EXAMPLE D4

3-[3-Methoxy-4-(2-pyrrolidin-1-yl-ethoxy)-phenyl]-2-methyl-6-phenoxy-3H-quinazolin-4-one A solution of 2-amino-N-[3-methoxy-4-(2-pyrrolidin-1-yl-ethoxy)-phenyl]-5-phenoxy-benzamide [Example D1] (25 mg, 0.055 mmol) in 1,2-dichloroethane (1 ml) was treated with triethylorthoacetate (2 ml) and the mixture heated to 80° C. for 2 hours. The mixture was cooled, 1 drop of DBU added and the mixture evaporated. The residue was subjected to flash chromatography on silica gel eluting with (methanol-dichloromethane-aqueous ammonia) to give the title compound;

$^1$H NMR (CDCl$_3$): δ 1.83 (4H, m), 2.27 (3H, s), 2.69 (4H, m), 3.01 (2H, t), 3.86 (3H, s), 4.23 (2H, t), 6.72 (1H, d), 6.77 (1H, dd), 7.00–7.06 (3H, m), 7.14 (1H, t), 7.36 (2H, dd), 7.48 (1H, dd), 7.67 (1H, d), 7.77 (1H, d); which crystallised as a white HCl salt on treatment with 1 M HCl in ether.

EXAMPLE D5

6-(4-Chloro-phenyl)-3-[3-methoxy-4-(2-pyrrolidin-1-yl-ethoxy)phenyl]-3H-quinazolin-4-one 4'-Chloro-4-nitro-biphenyl [J. Amer. Chem. Soc; 68; 1946; 404] (2.74 g, 11.7 mmol) was dissolved in DMF (20 ml) and THF (6 ml), then potassium t-butoxide 5.26 g (47 mmol) was added. The stirred mixture was cooled to −73° C. then a solution of chloroform in THF (6 ml) was slowly introduced, maintaining this temperature. After a further 1 minute, the reaction was quenched with acetic acid (5 ml). The mixture was poured into water (200 ml) and extracted with dichloromethane. The crude product was purified by flash chromatography on silica (using dichloromethane-hexane as eluents) to give 4'-chloro-3-(1,1-dichloro-methyl)-4-nitro-biphenyl in 63% yield;

$^1$H NMR (CDCl$_3$): δ 8.33 (s) 1H; 8.10 (d) 1H; 7.7 (d) 1H; 7.68 (s) 1H; 7.55 (d) 2H; 7.50 (d) 2H.

4'-Chloro-3-(1,1-dichloromethyl)-4-nitrobiphenyl (0.4 g, 1.26 mmol) was dissolved in methanolic sodium methoxide (15 mL; 0.5 M). The mixture was refluxed for 12 hours under argon. The solvent was evaporated and the residue diluted in 1,4-dioxane (15 ml) and water (1 ml), then a few drops of concentrated HCl were added. The reaction mixture was stirred at 100° C. for 4 hours. The solvent was then evaporated and the crude mixture purified by flash chromatography on silica gel (eluting with dichloromethane in petroleum ether) to yield the 4'-chloro-4-nitrobiphenyl-3-carbaldehyde (0.32 g, 1.26 mmol); m/z (APCI−) 260 (40%, [M−H]−), 231 (100%). This aldehyde (0.32 g, 1.26 mmol) was dissolved in acetic acid (5 mL) and sodium perborate (0.23 g, 1.5 mmol) was added. The resulting mixture was stirred at 50° C. for 16 h. The mixture was cooled, the solvent was evaporated, ethyl acetate was added and the organic layer washed with water, dried over MgSO$_4$ and evaporated to yield the 4'-chloro-4-nitrobiphenyl-3-carboxylic acid (0.14 g, 41%); m/z [APCI−] 276 (100%, [M−H−], 247 (60%).

This acid (0.14 g, 0.5 mmol) was dissolved in dichloromethane (2 ml) and oxalyl chloride added (87 μl, 1 mmol). The mixture was stirred for 60 min at room temperature under argon. The solvent was evaporated and the residue added to a solution of 3-methoxy-4-(2-pyrrolidin-1-ylethoxy)phenylamine [Example A4] (0.10 g, 0.44 mmol) and triethylamine (70 μl, 0.5 mmol) in dichloromethane (4 ml). The mixture was stirred for 90 mins at room temperature under argon and then washed with a saturated aqueous solution of NaHCO$_3$ (5 ml) and brine (5 ml). The organic layer was dried over MgSO$_4$, the solvent evaporated and the residue purified by flash chromatography on silica gel (eluting with methanol-dichloromethane-aq. ammonia). 4'-Chloro-4-nitrobiphenyl-3-carboxylic acid [3-methoxy-4-(2-pyrrolidin-1-ylethoxy)phenyl]amide was obtained in 54% yield; m/z [APCI+] 496 (100%, M+H+). Iron powder (45 mg, 0.81 mmol) and ammonium chloride (72 mg, 1.35 mmol) were mixed in water (2 ml) and 4'-chloro-4-nitrobiphenyl-3-carboxylic acid [3-methoxy-4-(2-pyrrolidin-1-ylethoxy)phenyl]amide (0.13 g, 0.27 mmol) added, dissolved in MeOH (2 ml). The mixture was heated at 80° C. for 90 min and then filtered while hot. Dichloromethane (30 ml) was added to the cooled filtrate. The organic layer was washed with water (10 ml), saturated aqueous NaHCO$_3$ (10 ml) and brine (10 ml), then dried and the solvent evaporated to give a yellow gum. This was dissolved in 1,2-dichloroethane (10 ml) and triethylorthoformate (4 ml). The mixture was refluxed for 16 h under argon, then after cooling DBU (0.2 ml) was added and the mixture was stirred for 10 mins at room temperature. The solvent was evaporated and the residue purified by flash chromatography on silica gel (eluting with methanol-dichloromethane-aqueous ammonia) to yield the title compound as an orange gum;

$^1$H NMR (CDCl$_3$): δ 1.78–1.86 (m, 4H), 2.65–2.78 (m, 4H), 2.99 (t, 2H), $$ 3.89 (s, 3H), 4.22 (t, 2H), 6.92–6.95 (m, 2H), 7.03 (d, 1H), 7.45 (d, 2H), 7.63 (d, 2H), $$ 7.83 (d, 1H), 8.00 (d, 1H), 8.13 (s, 1H), 8.54 (s, 1H);

which was converted to the hydrochloride salt by treatment with a solution of HCl in ether.

EXAMPLE E1

3-[3-Methoxy-4-(2-pyrrolidin-yl-ethoxy)-phenyl]-6-phenyl-3H-thieno[2,3-d]1triazine-4-one 6-Phenyl-3H-thieno[2,3-d][1,2,3]-triazinone (Indian Journal of Chemistry, 9, 1971, 1209), (100 mg, 0.44 mmol) and 3-methoxy(4-pyrrolidin-1-ylethoxy)phenylamine (103 mg, 0.44 mMol) [Example A4] were refluxed in xylene (5 ml) for 16 h. The solvent was evaporated and the residue purified by chromatography on deactivated neutral alumina (eluting with ethyl acetate-methanol) to give 2-amino-5-phenyl-thiophene-3-carboxylic acid [3-methoxy-4-(2-pyrrolidin-1-yl-ethoxy)-phenyl]-amide in 38% yield;

$^1$H NMR (CDCl$_3$): δ 10.7 (bs, 1H), 9.4 (s, 1H), 7.90 (s, 1H), 7.62 (s, 2H), 7.51 (d, 1H), 7.48 (d, 2H), 7.39 (t, 2H), 7.3 (dd, 1H), 7.18 (t, 1H), 7.01 (d, 1H), 4.29 (t, 2H), 3.80 (s, 3H), 3.51 (m, 4H), 1.98 (m, 4H); m/z [ES+], 438, [ES–] 436.

This material (50 mg, 0.114 mmol) was treated with butyl nitrite (1 ml) in dichlomethane (5 ml) at room temperature. The crude product was purified by flash chromatography on silica gel (eluting with dichloromethane-methanol-aq. ammnonia) to give the title compound;

$^1$H NMR (CDCl$_3$): δ 7.87 (s, 1H), 7.75 (d, 2H), 7.49 (m, 3H), 7.18 (dd, 1H), 7.15 (dd, 1H), 7.05 (d, 1H), 4.26 (t, 2H), 3.91 (s, 3H), 3.01 (t, 2H), 3.67 (m, 4H), 1.82 4H.

EXAMPLE E2

3-[3-Methoxy-4-(2-pyrrolidin-yl-ethoxy)-phenyl]-6-phenyl-3-H-thieno-[2,3-d]pyrimidin-4-one 2-Amino-5-phenyl-thiophene-3-carboxylic acid [3-methoxy-4-(2-pyrrolidin-1-yl-ethoxy)phenyl]-amide [Example E1] (28 mg, 0.064 mmol) was stirred at 95° C. in triethyl orthoformate (5 ml) for 24 h. The mixture was cooled, 4 drops of DBU added and the volatiles removed. The crude product was purified by chromatography on silica gel (eluting with dichloromethane-methanol-aq. ammonia) to give the title compound.

$^1$H NMR (CDCl$_3$): δ 8.06 (s, 1H), 7.73 (s, 1H) 7.68 (d, 2H) 7.42 (t, 3H), 7.35 (t, 1H), 7.01 (d, 1H), 6.92 (s, 1H) 4.23 (t, 2H), 3.92 (s, 3H), 3.00 (t, 2H), 2.68 (m, 4H), 1.84 (m, 4H).

EXAMPLE F1

3-[3-Methoxy-4-(2-pyrrolidin-1-yl-ethoxy)-phenyl]-6-phenyl-3H-thieno[3,2-d]pyrimidin-4-one A solution of 3-[3-methoxy-4-(2-pyrrolidin-1-ylethoxy) phenyl]-2-(methylthio)-6-phenylthieno[3,2-d]pyrimidin-4 (3H)-one [Example F2] 80 mg (0.16 mmol) in ethanol (10 ml) was treated with Raney Nickel [W10, 50 mg] with stirring at room temperature for 1 h. The solvent was evaporated and the residue purified by reverse phase preparative chromatography (using acetonitrile-water-TFA) to give the title compound as a trifluoroacetate salt;

$^1$H NMR (CDCl$_3$): δ 8.25 (bs, 1H), 7.76 (d, 2H), 7.61 (m, 2H), 7.50 (m, 3H), 7.05 (d, 1H), 6.98 (d, 1H), 6.94 (dd, 1H), 4.46 (t, 2H), 4.00 (m, 2H), 3.89 (s, 3H), 3.64 (t, 2H), 3.12 (m, 2H) 2.18 (m, 4H) 448

EXAMPLE F2

3-[3-methoxy-4-(2-pyrrolidin-1-ylethoxy)phenyl]-2-(methylthio)-6-phenylthieno[3,2-d]pyrimidin-4(3H)-one 5-Phenyl 3-amino thiophenecarboxylic acid methyl ester [Lancaster] (2 g, 8.54 mMol) and 2,2' Bis pyridyl thionate [Aldrich] (2 g, 8.54 mmol) were dissolved in dichloromethane (20 ml) then a solution of 3-methoxy(4-pyrrolidin-1-ylethoxy)phenylamine [Example A4] in dichloromethane (20 ml) introduced. The mixture was stirred for 2 hours at room temperature, then the solvent removed and the product purified by chromatography on silica gel (eluting with methanol-dichloromethane), to give 3-{3-[3-methoxy-4-(2-pyrrolidin-1-yl-ethoxy)-phenyl]-thioureido}-5-phenyl-thiophene-2-carboxylic acid methyl ester in 52% yield;

$^1$H NMR (CDCl$_3$): δ 10.60 (s, 1H), 9.14 (s, 1H), 7.90 (s, 1H), 7.65 (d, 2H), 7.40 (m, 3H), 6.97 (d, 1H), 6.88 (m, 2H), 4.20 (t, 2H), 3.89 (s, 3H), 3.73 (s, 3H), 2.98 (t, 2H), 2.66 (m, 4H), 1.83 (m, 4H). m/z 512 (ES+) 510 (ES–).

This ester (300 mg, 0.56 mmol) and potassium carbonate (162 mg, 1.17 mmol) were suspended in dry DMF (5 ml) and treated with a solution of methyl iodide (83 mg, 0.59 mmol) in DMF (1 ml). When the addition was complete, the mixture was evaporated. The residue was purified by chromatography on silica gel (eluting with dichloromethane-methanol) giving the title compound in 50% yield;

$^1$H NMR (CDCl$_3$): δ 7.72 (d, 2H), 7.45 (m, 4H), 7.05 (d, 1H), 6.90 (dd, 1H), 6.81 (d, 1H), 4.52 (m, 1H), 4.41 (m, 1H), 3.87 (s, 3H), 3.37 (m, 2H), 3.21 (m, 4H), 3.52 (s, 3H), 2.08 (m, 4H).

EXAMPLE F3

3-[3-Methoxy-4-(pyrrolidin-1-yl-ethoxy)phenyl-6-phenyl-2-thioxo-2,3-dihydro-1H-thieno[3,2-d]pyrimidin-4-one 3-{3-[3-Methoxy-4-(2-pyrrolidin-1-yl-ethoxy)-phenyl]-thioureido}-5-phenyl-thiophene-2-carboxylic acid methyl ester [Example F2] (100 mg, 0.2 mmol) was refluxed in toluene (10 ml) for 16 hours. The product was collected from the cooled solution by filtration in 42% yield;

$^1$H NMR (CDCl$_3$): δ 7.80 (m, 2H), 7.50 (m, 4H), 7.03 (d, 1H), 6.90 (d, 1H), 6.75 (dd, 1H), 4.14 (t, 2H), 3.73 (s, 3H), 2.98 (t, 2H), 2.70 (m, 4H), 1.76 (m, 4H); m/z [ES+] 480; (ES–) 478.

EXAMPLE G1

2-[3-Methoxy-4-(3-pyrrolidin-1-yl-propyl)-phenyl]-5-phenoxy-isoindole-1,3-dione 6-Nitroindanone [J. Med. Chem., 19, 1976, 472–475] (900 mg, 5.0 mmol) was suspended in dichloromethane (25 ml) and trifluoromethanesulphonic acid (0.05 ml) added. The resulting solution was cooled on ice. In a second flask, m-chloroperoxybenzoic acid [55%, Aldrich] (10 g) was suspended in dichloromethane and stirred for several minutes. The insoluble material was removed by filtration through a hydrophobic membrane and the filtrate evaporated to give a white powder. A portion of this material (2.6 g) was added portionwise to the indanone and the resultant suspension stirred for 72 h at room temperature. The reaction mixture was diluted with dichloromethane (10 ml) and aqueous sodium disulphite (20%; 10 ml). The aqueous layer was extracted (30 ml×3) with dichloromethane and the combined organic layers washed with saturated aqueous sodium bicarbonate (20 ml), brine (10 ml), and dried (MgSO$_4$) to yield crude 7-nitro-chroman-2-one as a brown solid (1.1 g, ~70% pure);

$^1$H NMR (CDCl$_3$): δ 8.01 (dd, 1H), 7.91 (dd, 1H), 7.40 (d, 1H,), 3.14 (d, 2H,), 2.86 (d, 2H,).

The crude 7-nitro-chroman-2-one (1.1 g, approx. 4.2 mmol) was dissolved in tetrahydrofuran (15 ml). Pyrrolidine (0.35 ml) was added and the reaction mixture stirred for 1 hour. The solution was adsorbed onto silica and eluted using methanol in dichloromethane. 3-(2-hydroxy-4-nitrophenyl)-1-pyrrolidin-1-yl-propan-1-one was obtained as a brown solid (900 mg, 3.40 mmol);

$^1$H NMR (CDCl$_3$): δ 10.62 (br, 1H); 7.74 (d, 1H); 7.66 (dd, 1H); 7.17 (d, 1H); 3.47 (m, 2H); 3.36 (m, 2H); 3.00 (m, 2H); 2.70 (m, 2H); 1.92 (m, 4H); MS (ES+) 265.2 (M+H$^+$; 100%).

This amide (900 mg, 3.4 mmol) was dissolved in dimethylformamide (100 ml) and potassium carbonate (516 mg) added, followed by iodomethane (0.6 ml, 3.7 mmol). The solution was stirred for 5 hours, then concentrated in vacuo. The residual oil was partitioned between ethyl acetate (50 ml) and H$_2$O (50 ml), the aqueous layer extracted with ethyl acetate (3×50 ml), the combined organic phases washed with brine (20 ml), dried (MgSO$_4$) and evaporated to yield 3-(2-methoxy-4-nitrophenyl)-1-pyrrolidin-1-yl-propan-1-one as a black oil (900 mg, 3.2 mmol);

$^1$H NMR (CDCl$_3$): δ 7.78 (dd, 1H, J=8.2 Hz, 2.2 Hz); 7.68 (d, 1H, J=2.2 Hz); 7.36 (d, 1H, J=8.2 Hz); 3.93 (s, 3H); 3.46 (t, 4H, J=6.6 Hz); 3.34 (t, 2H, J=7.7 Hz); 2.55 (t, 2H, J=7.7 Hz); 1.89 (m, 4H)

This amide (900 mg, 3.2 mmol) was dissolved in tetrahydrofuran (150 ml) and treated with borane:tetrahydrofuran (1M, 10 ml). The reaction mixture was heated to 50° C. for 4 hours, followed by a further addition of borane:THF solution (10 ml). After heating for a further 16 hours, a third portion (10 ml) was added, and heating maintained for a further 3 hours. The reaction mixture was cooled and methanol (10 ml) added, followed by conc. hydrochloric acid (0.5 ml). The mixture was heated to 80° C. for 1 hour, then evaporated in vacuo. The residue was partitioned between ethyl acetate (50 ml) and H$_2$O (50 ml), the aqueous phases extracted with ethyl acetate (3×50 ml) and the combined organics washed with brine (20 ml), dried (MgSO$_4$) and evaporated. The resultant crude brown oil was purified by chromatography on silica gel using methanol in dichloromethane as eluent. 1-[3-(2-methoxy-4-nitrophenyl)-propyl]-pyrrolidine was obtained as a clear oil (186 mg, 22%);

$^1$H NMR (CDCl$_3$): δ 7.80 (dd, 1H,); 7.78 (d, 1H); 7.29 (d, 1H); 3.93 (s, 3H); 3.20 (m, 2H); 2.82 (m, 2H); 2.68 (m, 4H); 2.16 (m, 4H); 1.86 (m, 2H).

This amine (186 mg, 0.7 mmol) was dissolved in 4:1 mixture of ethanol:THF (20 ml), and palladium on carbon (10% wet paste; 100 mg) added. The mixture was stirred under an atmosphere of hydrogen for 16 h, then filtered over filter-aid and evaporated to yield 3-methoxy-4-(3-pyrrolidin-1-yl-propyl)-phenylamine as a colourless oil (148 mg, 90%);

$^1$H NMR (CDCl$_3$):δ 6.88 (m, 1H); 6.21 (m, 2H); 3.74 (s, 3H); 3.61 (br, 2H); 2.49 (m, 8H); 1.77 (m, 6H).

This amine was used in place of 3-methoxy-4-(3-pyrrolidin-1-yl-propyl)-phenylamine in using the procedure of Example A4 to give 2-[3-methoxy-4-(3-pyrrolidin-1-yl-propyl)-phenyl]-5-phenoxy-isoindole-1,3-dione.

EXAMPLE G2

4-(1,3-Dioxo-5-phenoxy-1,3-dihydro-isoindol-2-yl)-2-methoxymethoxy-N-(2-pyrrolidin-1-yl-ethyl)-benzamide A solution of 2-chloro-4-nitrophenol [Specs] (345 mg, 2 mmol) in DMF (5 ml) was treated with sodium hydride (60% oil dispersion, 140 mg, 3.5 mmol), then chloromethylmethyl ether (193 mg, 182 ul, 2.4 mmol). The mixture was stirred for 24 h then methanol (5 ml) added, the mixture stirred for a further 1 h then evaporated, the residue dissolved in dichloromethane, filtered, evaporated and the residue purified by flash chromatography (diethyl ether-hexane) to afford 1-chloro-2-methoxymethoxy-4-nitro-benzene as a clear oil;

$^1$H NMR (CDCl$_3$): δ 3.55 (3H, s), 5.35 (2H, s), 7.53 (1H, d), 7.84 (1H, dd), 8.05 (1H, d).

This material (445 mg, 2.05 mmol) was dissolved in DMF (5 ml) and treated with N-2-hydroxyethylpyrrolidine (288 mg, 2.5 mmol), and sodium hydride (60% oil dispersion, 90 mg, 2.3 mmol), added. The mixture was heated to 80° C. for 8 hours then cooled and stirred at RT for 30 h. The solvent was removed in vacuo, and the residue subjected to flash chromatography (aq. ammonia-methanol-dichloromethane) to afford 1-[2-(2-methoxymethoxy-4-nitro-phenoxy)-ethyl]-pyrrolidine as a waxy solid (449 mg, 1.5 mmol).

$^1$H NMR (CDCl$_3$): δ 1.81 (4H, m), 2.66 (4H, m), 2.97 (2H, t), 3.53 (3H, s), 4.25 (2H, t), 5.26 (2H, s), 6.95 (1H, d), 7.94 (1H, dd), 8.00 (1H, d).

This material (449 mg, 1.5 mmol) was dissolved in ethanol (30 ml) and hydrogenated on 10% Pd on carbon (100 mg) for 6 hours at RTP. The catalyst was removed by filtration and the filtrate evaporated to give 3-methoxymethoxy-4-(2-pyrrolidin-1-yl-ethoxy)-phenylamine as a white solid;

$^1$H NMR (CDCl$_3$): δ 1.80 (4H, m), 2.64 (4H, m), 2.86 (2H, t), 3.4 (2H, brs), 3.50 (3H, s), 4.07 (2H, t), 5.16 (2H, s), 6.28 (1H, dd), 6.54 (1H, d), 6.76 (1H, d)

This material was treated with 3-phenoxyphthalic anhydride in the same manner as for 4-(2-diisopropylamino-ethoxy)-3-methoxy-phenylamine in Example A4 to give the title compound, which crystallised from dilute TFA in ether as a trifluoroacetate salt.

EXAMPLE G3

2-[3-(2-Methoxy-ethoxy)-4-(2-pyrrolidin-1-yl-ethoxy)-phenyl]-5-phenoxy-isoindole-1,3-dione 2-Chloro-4-nitrophenol was treated with 2-methoxyethyl chloride [Aldrich] in place of chloromethyl methyl ether in the procedure of Example G2 to give the title compound, which crystallised from dilute TFA in ether as a trifluoroacetate salt.

EXAMPLE G4

2-[3-Methoxymethyl-4-(2-pyrrolidin-1-yl-ethoxy)-phenyl]-5-phenoxy-isoindole-1,3-dione 1-Chloro-2-methoxymethyl-4-nitro-benzene [U.S. Pat. No. 5,084,449 A] was utilised in place of 1-chloro-2-methoxymethoxy-4-nitro-benzene in the procedure of Example G2 to afford the title compound as a white solid as the trifluoroacetate salt.

EXAMPLE G5

2-[3-Hydroxy-4-(2-pyrrolidin-1-yl-ethoxy)-phenyl]-5-phenoxy-isoindole-1,3-dione 4-(1,3-Dioxo-5-phenoxy-1,3-dihydro-isoindol-2-yl)-2-methoxymethoxy-N-(2-pyrrolidin-1-yl-ethyl)-benzamide [Example G2] was treated with trifluoroacetic acid (1 ml, 1 M in dichloromethane). After 30 minutes, the solvent was removed to afford the title compound as a trifluoroacetate salt.

EXAMPLE G6

2-{4-[2-(2,5-Dimethyl-pyrrolidin-1-yl)-ethoxy]-3-methoxy-phenyl}-5-phenoxy-isoindole-1,3-dione 2,5-dimethyl-pyrrolidine was treated in the same manner as azetidine in Example G11 to give first 1-(2,5-dimethyl-pyrrolidin-1-yl)-2-(2-methoxy-4-nitro-phenoxy)-ethanone;

$^1$H NMR (CDCl$_3$): δ 7.86 (dd, 1H), 7.76 (d, 1H), 6.93 (d, 1H), 4.85 (bm, 2H), 4.12 (bm, 2H), 3.96 (s, 3H), 2.11 (bm, 1H), 1.99 (bm, 1H), 1.70 (bm, 2H), 1.30 (m, 6H).

This was treated in the same manner as 1-azetidin-1-yl-2-(2-methoxy-4-nitro-phenoxy)-ethanone [Example 19] to give 1-[2-(2-methoxy-4-nitro-phenoxy)-ethyl]-2,5-dimethyl-pyrrolidine;

$^1$H NMR (CDCl$_3$): δ 7.89 (dd, 1H), 7.74 (d, 1H), 6.92 (m, 1H), 4.16 (t, 2H), 3.94 (s, 3H), 2.71 (m, 2H), 1.87 (m, 2H), 1.39 (m, 2H), 1.15 & 1.05 (d, 6H).

This material was treated in the same manner as 1-[2-(2-methoxy-4-nitro-phenoxy)-ethyl]-azetidine in Example G11 to give the title compound (as a mixture of meso isomers and enantiomers).

EXAMPLE G7

2-{4-[2-(2-methyl-pyrrolidin-1-yl)-ethoxy]-3-methoxy-phenyl}-5-phenoxy-isoindole-1,3-dione 2-methylpyrrolidine was treated in the same manner as azetidine in Example G11 to give first 2-(2-methoxy-4-nitro-phenoxy)-1-(2-methyl-pyrrolidin-1-yl)-ethanone; $^1$H NMR (CDCl$_3$): δ 7.84 (dd, 1H), 7.75 (d, 1H), 6.94 (d, 1H), 4.79 (s, 2H), 4.23 (bm, 3H), 3.96 (s, 3H), 3.53 (bm, 2H), 1.96 (bm, 4H), 1.20 (d, 3H). This was treated in the same manner as 1-azetidin-1-yl-2-(2-methoxy-4-nitro-phenoxy)-ethanone [Example 19] to give 1-[2-(2-methoxy-4-nitro-phenoxy)-ethyl]-2-methyl-pyrrolidine;

$^1$H NMR (CDCl$_3$): δ 7.89 (dd, 1H), 7.74 (d, 1H), 6.92 (d, 1H), 4.24 (t, 2$$ H), 3.94 (s, 3H), 3.28 (m, 2H), 2.66 (q, 1H, J=6.5 Hz), 2.4 (m, 2H), 1.95 (m, 1H), 1.79 (m, 2H), 1.46 (m, 1H), 1.14 (d, 3H, J=6.07 Hz). This material was treated in the same manner as 1-[2-(2-methoxy-4-nitro-phenoxy)-ethyl]-azetidine in Example G11 to give the title compound.

EXAMPLE G8

2-{4-[2-(2-methyl-piperidin-1-yl)-ethoxy]-3-methoxy-phenyl}-5-phenoxy-isoindole-1,3-dione 2-Methylpiperidine was treated in the same manner as azetidine in Example G11 to give first 2-(2-methoxy-4-nitro-phenoxy)-1-(2-methyl-piperidin-1-yl)-ethanone; $^1$H NMR (CDCl$_3$): δ 7.85 (dd, 1H), 7.75 (d, 1H), 6.97 (d, 1H), 4.88 (s, 2H), 3.96 (s, 3H), 1.72–1.65 (bm, 6H), 1.30–1.13 (bm, 6H); m/z [AP+] 309.2 (MH$^+$, 100%). This was treated in the same manner as 1-azetidin-1-yl-2-(2-methoxy-4-nitro-phenoxy)-ethanone [Example 19] to give 1-[2-(2-methoxy-4-nitro-phenoxy)-ethyl]-2-methyl-piperidine.

$^1$H NMR (CDCl$_3$): δ 7.86 (dd, 1H), 7.76 (d, 1H), 6.93 (d, 1H), 4.91 (bm, 2H), 3.96 (s, 3H), 1.85 (bm, 2H), 1.63 (bm, 4H), 1.56–1.50 (bm, 2H), 1.32–1.21 (bm, 6H); m/z [AP+] 323.2 (MH$^+$, 100%). This material was treated in the same manner as 1-[2-(2-methoxy-4-nitro-phenoxy)-ethyl]-azetidine in Example G11 to give the title compound.

EXAMPLE G9

2-{4-[2-((cis)-2,6-dimethyl-piperidin-1-yl)-ethoxy]-3-methoxy-phenyl}-5-phenoxy-isoindole-1,3-dione 2,5-(cis)-Dimethylpiperidine was treated in the same manner as azetidine in Example G11 to give first 1-[2-(2-methoxy-4-nitro-phenoxy)-ethyl]-(cis)-2,6-dimethyl-piperidine; $^1$H NMR (CDCl$_3$): δ 7.89 (dd, 1H), 7.74 (d, 1H), 6.94 (d, 1H), 4.21 (t, 2H), 3.94 (s, 3H), 3.17 (q, 1H), 2.95 (m, 1H), 2.84 (q, 1H), 2.39 (m, 2H), 1.65 (m, 4H), 1.33 (m, 2H), 1.12 (d, 3H).

This was treated in the same manner as 1-azetidin-1-yl-2-(2-methoxy-4-nitro-phenoxy)-ethanone [Example 19] to give 1-[2-(2-methoxy-4-nitro-phenoxy)-ethyl]-(cis)-2,6-dimethyl-piperidine;

$^1$H NMR (CDCl$_3$): δ 7.89 (dd, 1H), 7.74 (d, 1H), 6.91 (d, 1H), 4.09 (t, 2H), 3.93 (s, 3H), 3.11 (t, 2H), 2.56 (m, 2H), 1.69 (m, 1H), 1.55 (bm, 2H), 1.32 (m, 3H), 1.18 (d, 6H). This material was treated in the same manner as 1-[2-(2-methoxy-4-nitro-phenoxy)-ethyl]-azetidine in Example G11 to give the title compound.

EXAMPLE G10

2-(4-[2-(2,2,6,6-tetramethyl-piperidin-1-yl)-ethoxy]-3-methoxy-phenyl)-5-phenoxy-isoindole-1,3-dione 2,2,6,6-Tetramethylpiperidine was treated in the same manner as azetidine in Example G11 to give first 2-(2-methoxy-4-nitro-phenoxy)-1-(2,2,6,6-tetramethyl-piperidin-1-yl)-ethanone;

$^1$H NMR (CDCl$_3$): δ 7.84 (dd, 1H), 7.75 (d, 1H), 6.86 (d, 1H), 4.84 (s, 2H), 3.96 (s, 3H), 1.77 (bm, 6H), 1.49 (s, 12H).

This was treated in the same manner as 1-azetidin-1-yl-2-(2-methoxy-4-nitro-phenoxy)-ethanone [Example 19] to give 1-[2-(2-methoxy-4-nitro-phenoxy)-ethyl]-2,2,6,6-tetramethyl-piperidine;

$^1$H NMR (CDCl$_3$): δ 7.89 (dd, 1H), 7.74 (d, 1H), 6.92 (d, 1H), 3.96 (m, 5H), 2.99 (t, 2H), 1.55 (bm, 2H), 1.08 (s, 12H).

This material was treated in the same manner as 1-[2-(2-methoxy-4-nitro-phenoxy)-ethyl]-azetidine in Example G11 to give the title compound.

EXAMPLE G11

2-[4-(2-Azetidin-1-yl-ethoxy)-3-methoxy-phenyl]-5-phenoxy-isoindole-1,3-dione A suspension of (2-methoxy-4-nitro-phenoxy)acetic acid [FEBS Lett. (1983), 153(2), 431], (3.12 g 15.9 mmol) in dichloromethane (100 ml) was cooled down to 0° C. in an ice bath before oxalyl chloride (5.26 g, 41.7 mmol) was added. The reaction mixture was stirred for 45 minutes, giving a clear solution. The solvents were removed in vacuo to give (2-methoxy-4-nitro-phenoxy)-acetyl chloride as a pale yellow solid. (3.41 g, 100%);

$^1$H NMR (CDCl$_3$): δ 7.87 (dd, 1H,), 7.81 (d, 1H), 6.92 (d, 1H), 5.09 (s, 2H), 3.98 (s, 3H).

A solution of this acid chloride (300 mg, 1.22 mmol) was dissolved in dichloromethane (12 ml) and treated with azetidine (76 mg, 1.34 mmol) followed by triethylamine (370 mg, 3.66 mmol). The reaction mixture was stirred at RT for 16 h under an argon atmosphere. The solvent was removed in vacuo to give a dark brown oil which was purified by flash chromatography on silica gel (eluting with dichloromethane-methanol-aqueous ammonia) to give 1-azetidin-1-yl-2-(2-methoxy-4-nitro-phenoxy)-ethanone as a yellow oil (150 mg, 46%);

$^1$H NMR (CDCl$_3$): 7.88 (dd, 1H), 7.77 (d, 1H), 6.91 (d, 1H), 4.70 (s, 2H), 4.37 (t, 2H), 4.11 (t, 2H), 3.96 (s, 3H), 2.34 (q, 2H).

This amide was dissolved in THF (15 ml) then borane (5.6 ml, 1M solution in THF) was introduced. The reaction mixture was stirred for 18 hours at 50° C. under argon. Excess borane was quenched by the dropwise addition of MeOH then aq HCl (2M, 200 ul). The solvent was removed in vacuo and the residual oil partitioned between ethyl acetate and a saturated solution of aqueous sodium bicarbonate (20 ml). The aqueous phase was extracted with ethyl acetate (3×50 ml). The combined ethyl acetate layers were washed with brine and dried over MgSO$_4$. The solvent was removed in vacuo to yield 1-[2-(2-methoxy-4-nitro-phenoxy)-ethyl]-azetidine as a pale red oil (53 mg, 38%);

$^1$H NMR (CDCl$_3$): 7.89 (dd, 1H, J=8.9), 7.73 (d, 1H), 6.89 (d, 1H), 4.09 (t, 2H), 3.93 (s, 3H), 3.35 (t, 4H), 2.91 (t, 2H), 2.13 (t, 2H).

1-[2-(2-methoxy-4-nitro-phenoxy)-ethyl]-azetidine (53.5 mg, 0.21 mmol) was dissolved in a 1:1 mixture of THF and ethanol (7 ml) and 10% palladium on carbon paste (150 mg) introduced. The reaction mixture was stirred under an atmosphere of hydrogen for 50 hours at RT. The catalyst was filtered off over filter-aid and the filtrate evaporated to give 4-[2-azetidin-1-yl-ethoxy]-3-methoxy-phenylamine as a brown oil (47 mg, 100%). This material was treated with 3-phenoxyphthalic anhydride in the same manner as for 4-(2-diisopropylamino-ethoxy)-3-methoxy-phenylamine in Example A4 to give the title compound.

EXAMPLE G12

2-{4-[2-(7-Aza-bicyclo[2.2]hept-7-yl)-ethoxy]-3-methoxy-phenyl}-5-phenoxy-isoindole-1,3-dione 7-Aza-bicyclo[2.2.1]heptane [J. Am. Chem. Soc. (1989), 111(5), 1776–81], was treated in the same manner as azetidine in Example G11 to give the title compound.

EXAMPLE G13

2-{4-[2-(2-Aza-bicyclo[2.2.2] oct-2-yl)ethoxy]-3-methoxy-phenyl}-5-phenoxy-isoindole-1,3-dione 2-Aza-bicyclo[2.2.2]octane [J. Am. Chem. Soc. (1989), 111(5), 1776–81], was treated in the same manner as azetidine in Example G11 to give the title compound.

EXAMPLE G14

2-[3-Methoxy-4-[2-(4-phenyl-piperidin-1-yl) ethoxy]-phenyl)-5-phenoxy-isoindole-1,3-dione 4-Phenylpiperidine [AstaTech] was treated in the same manner as azetidine in Example G11 to give the title compound.

EXAMPLE G15

5-Phenoxy-2-(2-pyrrolidin-1-ylmethyl-2,3-dihydro-benzo[1,4]dioxin-6-yl)-isoindole-1,3-dione 2-Pyrrolidin-1-ylmethyl-2,3-dihydro-benzo[1,4]dioxin-6-ylamine (WO 0121577 A2] was treated with 3-phenoxyphthalic anhydride in the same manner as for 4-(2-diisopropylamino-ethoxy)-3-methoxy-phenylamine in Example A4 to give the title compound.

EXAMPLE G16

Dimethyl-[7-(5-phenoxy-1,3-dihydro-isoindol-2-yl)-chroman-3-ylmethyl]-amine

3-Dimethylaminomethyl-chroman-7-ylamine[WO 0121577 A2] was treated with 3-phenoxyphthalic anhydride in the same manner as for 4-(2-diisopropylamino-ethoxy)-3-methoxy-phenylamine in Example A4 to give the title compound.

EXAMPLE G17

5-Phenoxy-2-(6-pyrrolidin-1-ylmethyl-5,6,7,8-tetrahydro-naphthalen-2-yl)-isoindole-1,3-dione 6-Pyrrolidin-1-ylmethyl-5,6,7,8-tetrahydro-naphthalen-2-ylamine [WO 0121577 A2] was treated with 3-phenoxyphthalic anhydride in the same manner as for 4-(2-diisopropylamino-ethoxy)-3-methoxy-phenylamine in Example A4 to give the title compound.

EXAMPLE G18

5-Phenoxy-2-(3-Pyrrolidin-1-ylmethyl-2H-chromen-7-yl)-isoindole-1,3-dione

3-Pyrrolidin-1-ylmethyl-2H-chromen-7-ylamine [WO 0121577 A2] was treated with 3-phenoxyphthalic anhydride in the same manner as for 4-(2-diisopropylamino-ethoxy)-3-methoxy-phenylamine in Example A4 to give the title compound.

EXAMPLE G19

5-Phenoxy-2-(6-pyrrolidin-1-ylmethyl-7,8-dihydro-naphthalen-2-yl)-isoindole-1,3-dione 6-Pyrrolidin-1-ylmethyl-7,8-dihydro-naphthalen-2-ylamine [WO 0121577 A2] was treated with 3-phenoxyphthalic anhydride in the same manner as for 4-(2-diisopropylamino-ethoxy)-3-methoxy-phenylamine in Example A4 to give the title compound.

EXAMPLE G20

2-{3-Methoxy-4-[3-(4-phenyl-piperidin-1-yl)-propoxy]-phenyl}-5-phenoxy-isoindole-1,3-dione 4-Phenyl-piperidine [Aldrich] was treated in the same manner as pyrrolidine in the procedure of Example G21 to give the title compound.

EXAMPLE G21

2-[3-Methoxy-4-(3-pyrrolidin-1-yl-propoxy)-phenyl]-5-phenoxy-isoindole-1,3-dione A solution of 3-bromo-1-propanol (0.685 g, 4.93 mmol), 4-nitroguaiacol (1 g, 5.91 mmol) and tributylphosphine (1.49 g, 7.36 mmol) in 20 ml tetrahydrofuran was treated with 1,1'-(azodicarbonyl)dipiperidine (1.49 g, mmol), added portionwise over 5 mins, and the resulting mixture stirred for 16 hrs. The solvent was removed in vacuo and the residues partitioned between ethyl acetate (25 ml) and 0.5 M HCl (25 ml). The organic phase was washed with 0.5 M NaOH (4×25 ml), water (25 ml) and saturated brine (25 ml), then dried and concentrated to a pale yellow solid. This was purified by flash chromatography on silica gel (eluting with ethyl acetate-hexane) to give 1-(3-bromo-propoxy)-2-methoxy-4-nitro-benzene as a white solid (300 mg, 21%);

$^1$H NMR (DMSO) δ 2.26–2.33 (m, 2H), 3.64–3.67 (t, 2H), 3.89 (s, 3H), 4.21–4.24 (t, 2H), 7.20–7.23 (d, 1H), 7.74–7.75 (d, 1H), 7.88–7.91 (dd, 1H).

This material (100 mg, 0.34 mmol) was treated with pyrrolidine (27 mg, 0.37 mmol) and potassium carbonate (96.7 mg, 0.68 mmol) in DMF (10 ml). The mixture was heated to 70° C. for 16 hrs and the resulting solution partitioned between water (25 ml) and ethyl acetate (25 ml). The organic phase was extracted and washed with water (10 ml) and brine (5 ml), then dried (MgSO$_4$) and concentrated to yield 1-[3-(2-methoxy-4-nitro-phenoxy)-propyl]-pyrrolidine as a yellow oil (90 mg, 94%);

$^1$H-NMR (DMSO) δ1.66–1.70 (m, 4H), 1.89–1.96 (m, 2H), 2.44–2.55 (m 6H), 3.88(s, 3H), 4.14–4.18 (t, 2H), 7.17–7.19 (d, 1H), 7.73–7.75 (d, 1H), 7.87–7.9 (dd, 2H).

This amine (90 mg, 0.32 mmol), was dissolved in ethanol (5 ml) and treated with 10% palladium on carbon (40 mg) then the mixture stirred under a hydrogen atmosphere for 16 hrs. The mixture was filtered through a plug of celite and the filtrate concentrated to yield 3-methoxy-4-(3-pyrrolidin-1-yl-propoxy)-phenylamine as a brown oil (75 mg, 93%);

$^1$H-NMR (DMSO) δ 1.66–1.69 (m, 4H), 1.76–1.79 (m, 2H), 2.44 (bm, 6H), 3.66 (s, 3H), 3.79–3.82 (t, 2H), 4.64 (bs, 2H), 6.02–6.05 (dd, 1H), 6.24–6.25 (d, 1H), 6.61–6.63 (d, 1H). This aniline was treated with 3-phenoxyphthalic anhydride in the same manner as for 4-(2-diisopropylamino-ethoxy)-3-methoxy-phenylamine in Example A4 to give the title compound.

EXAMPLE G22

2-{3-Methoxy-4-[3-(4-methyl-piperazin-1-yl)-propoxy]-phenyl}-5-phenoxy-isoindole-1,3-dione N-methyl-piperazine [Aldrich] was treated in the same manner as pyrrolidine in the procedure of Example G21 to give the title compound.

EXAMPLE G23

2-[4-(3-Azepan-1-yl-propoxy)$_3$-methoxy-phenyl]-5-phenoxy-isoindole-1,3-dione

Hexamethyleneamine [Aldrich] was treated in the same manner as pyrrolidine in the procedure of Example G21 to give the title compound.

EXAMPLE G24

2-[3-Methoxy-4-(3-morpholin-4-yl-propoxy)-phenyl]-5-phenoxy-isoindole-1,3-dione

Morpholine [Aldrich] was treated in the same manner as pyrrolidine in the procedure of Example G21 to give the title compound.

The following tables give examples which illustrate but do not limit the invention in any way.

TABLE A

Encompassing compounds of general formula (A), a subset of formula (I) where QY = a phthalimide group, $R^6$ = OMe and ML is an oxyethyl group

| Example No. | R$^1$/R$^2$ | Z | R3 | [M + H] + (AP+) |
|---|---|---|---|---|
| A1 | —O—CH$_2$CH$_2$—N(iPr)(iPr) | bond | Ph | 473 |
| A2 | —O—CH$_2$CH$_2$—N(iPr)(iPr) | CH$_2$ | Ph | 487 |
| A3 | —O—CH$_2$CH$_2$—N(iPr)(iPr) | NH | Ph | 488 |
| A4 | —O—CH$_2$CH$_2$-pyrrolidinyl | O | Ph | 459 |
| A5 | —O—CH$_2$CH$_2$-pyrrolidinyl | NH | Ph | 458 |
| A6 | —O—CH$_2$CH$_2$-pyrrolidinyl | CH$_2$ | Ph | 457 |
| A7 | —O—CH$_2$CH$_2$-pyrrolidinyl | S | Ph | 475 |
| A8 | —O—CH$_2$CH$_2$-pyrrolidinyl | S | p-Cl—Ph | 509, 511 |
| A9 | —O—CH$_2$CH$_2$-pyrrolidinyl | S | 3-MeO—Ph | 505 |
| A10 | —O—CH$_2$CH$_2$-pyrrolidinyl | S | 4-HO—Ph | 491 |
| A11 | —O—CH$_2$CH$_2$-pyrrolidinyl | S | 4-F—Ph | 493 |
| A12 | —O—CH$_2$CH$_2$-pyrrolidinyl | S | 4-H$_2$N—Ph | 490 |

TABLE A-continued

Encompassing compounds of general formula (A), a subset of formula (I) where QY = a phthalimide group, $R^6$ = OMe and ML is an oxyethyl group (A)

| Example No. | $\cdots O\diagdown N\diagup R^1 \diagdown R^2$ | Z | R3 | [M + H]+ (AP+) |
|---|---|---|---|---|
| A13 | O-ethyl-pyrrolidine | S | 4-F$_3$C—Ph | 543 |
| A14 | O-ethyl-pyrrolidine | S | 4-MeO—Ph | 505 |
| A15 | O-ethyl-pyrrolidine | O | 4-Cl—Ph | 493, 495 |
| A16 | O-ethyl-pyrrolidine | O | 4-F—Ph | 477 |
| A17 | O-ethyl-pyrrolidine | O | 4-F$_3$C—Ph | 527 |
| A18 | O-ethyl-pyrrolidine | O | 4-F-3-Cl—Ph | 561, 563 |
| A19 | O-ethyl-pyrrolidine | O | 3-Fl—Ph | 477 |
| A20 | O-ethyl-pyrrolidine | O | 3-Cl—Ph | 493, 495 |
| A21 | O-ethyl-pyrrolidine | O | 3-$^t$Bu—Ph | 515 |
| A22 | O-ethyl-pyrrolidine | O | 3-MeO—Ph | 489 |
| A23 | O-ethyl-pyrrolidine | O | 3-Me—Ph | 473 |
| A24 | O-ethyl-pyrrolidine | O | 4-Me—Ph | 473 |
| A25 | O-ethyl-pyrrolidine | O | 4-NC—Ph | 484 |
| A26 | O-ethyl-pyrrolidine | O | 2-NC—Ph | 484 |
| A27 | O-ethyl-pyrrolidine | O | 2-MeS—Ph | 505 |
| A28 | O-ethyl-pyrrolidine | O | 2-Br—Ph | 537, 539 |
| A29 | O-ethyl-pyrrolidine | O | 2-Cl—Ph | 493, 495 |
| A30 | O-ethyl-pyrrolidine | O | 2-F—Ph | 477 |
| A31 | O-ethyl-pyrrolidine | O | 2-Et—Ph | 487 |
| A32 | O-ethyl-pyrrolidine | O | 2,5-diF—Ph | 495 |
| A33 | O-ethyl-pyrrolidine | O | 2-F$_3$C—Ph | 527 |
| A34 | O-ethyl-pyrrolidine | O | 2,4-diF—Ph | 495 |
| A35 | O-ethyl-pyrrolidine | O | 4-F-2-MeO—Ph | 507 |
| A36 | O-ethyl-pyrrolidine | O | 2-MeO—Ph | 489 |
| A37 | O-ethyl-pyrrolidine | O | cyclohexenyl | 463 |

TABLE A-continued

Encompassing compounds of general formula (A), a subset of formula (I) where QY = a phthalimide group, $R^6$ = OMe and ML is an oxyethyl group

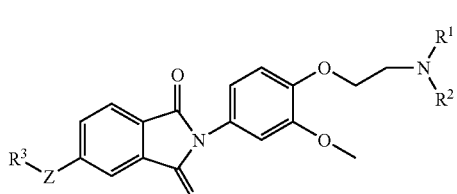
(A)

| Example No. | ⋯O⧹⧸N$R^1$$R^2$ | Z | R3 | [M + H]+ (AP+) |
|---|---|---|---|---|
| A38 | pyrrolidinylethoxy | O | propenyl | 451 |
| A39 | pyrrolidinylethoxy | O | 2-methylpropenyl | 451 |
| A40 | pyrrolidinylethoxy | O | isopropenyl | 437 |
| A41 | pyrrolidinylethoxy | O | cyclopentenyl | 449 |
| A42 | pyrrolidinylethoxy | O | cyclohexyl | 465 |
| A43 | pyrrolidinylethoxy | O | cyclopentyl | 451 |

TABLE B

Encompassing compounds of general formula B, a subset of formula (I) where QY = a benzene ring fused onto a 5-membered heterocycle composed of groups J, and J' and J" and linked via J"; $R^6$ = OMe, ML is an oxyethyl group and $R^3$ = Ph

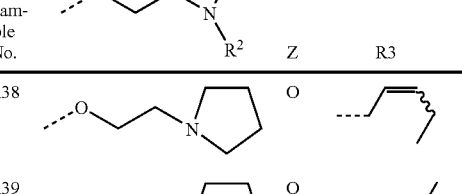
(B)

| Example No. | ⋯O⧹⧸N$R^1$$R^2$ | Z | J | J' | J" | [M + H]+ [AP+, 100%] |
|---|---|---|---|---|---|---|
| B1 | diisopropylamino-ethoxy | bond | C=O | CH$_2$ | N | 459 |
| B2 | diisopropylamino-ethoxy | bond | CH$_2$ | C=O | N | 459 |
| B3 | pyrrolidinylethoxy | O | C=O | CH$_2$ | N | 445 |

TABLE C

Encompassing compounds of general formula (C), a subset of formula (I) where QY = a benzene ring fused onto a 6-membered heterocycle composed of groups J, J', J" and J''' and linked via J'''; ML is an oxyethyl group and NR$^1$R$^2$ form a pyrrolidine ring.

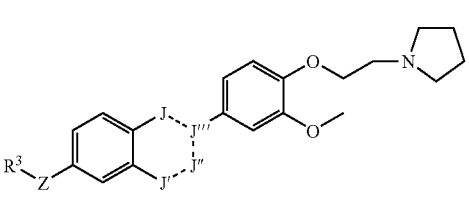
(C)

| Example No. | R$^3$ | Z | J | J' | J" | J''' | [M + H]+ [AP+, 100%] |
|---|---|---|---|---|---|---|---|
| C1 | Ph | O | C=O | N= | =N— | N | 459 |
| C2 | Ph | O | C=O | N= | =CH— | N | 458 |
| C3 | Ph | O | C=O | NH— | C=O | N | 474 |
| C4 | Ph | O | C=O | N= | =CMe— | N | 472 |
| C5 | Ph | bond | C=O | N= | =N— | N | 443 |
| C6 | Ph | bond | C=O | N= | =CH— | N | 442 |
| C7 | Ph | bond | C=O | NH— | C=O | N | 458 |
| C8 | Ph | bond | C=O | —N= | =CMe— | N | 456 |
| C9 | Allyl | O | C=O | N= | =CH— | N | 422 |

TABLE D

Encompassing compounds of general formula (D), a subset of formula (I) where QY = a benzene ring fused onto a 6-membered heterocycle composed of groups J, J', J" and J'" and linked via J'" ; ML is an oxyethyl group, $R^6$ = OMe

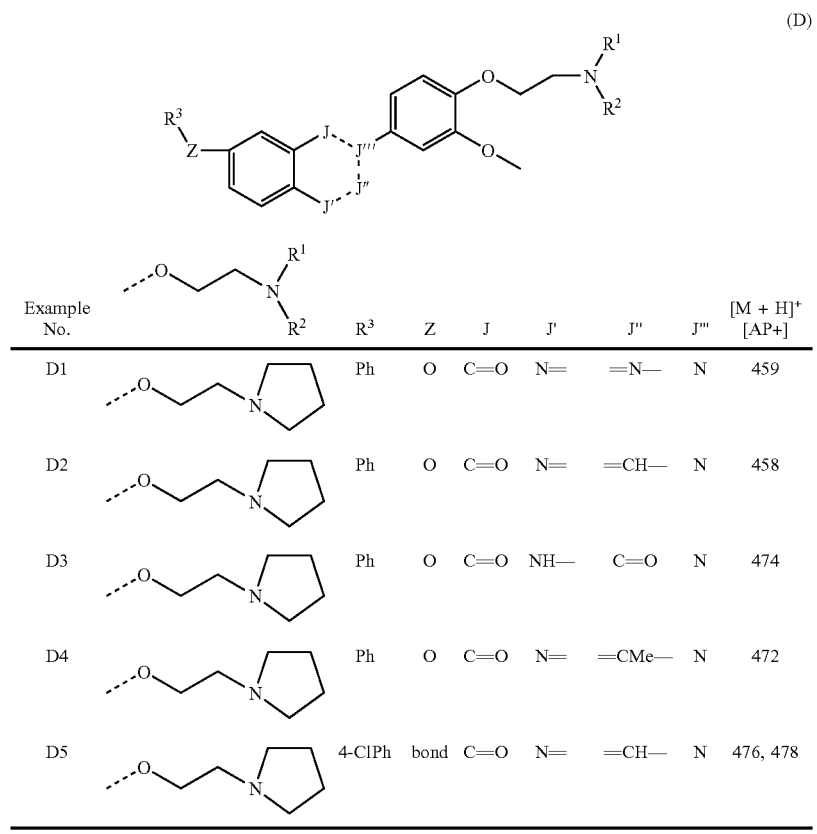

| Example No. | $R^1$ $R^2$ | $R^3$ | Z | J | J' | J" | J'" | [M + H]⁺ [AP+] |
|---|---|---|---|---|---|---|---|---|
| D1 | pyrrolidine-ethoxy | Ph | O | C=O | N= | =N— | N | 459 |
| D2 | pyrrolidine-ethoxy | Ph | O | C=O | N= | =CH— | N | 458 |
| D3 | pyrrolidine-ethoxy | Ph | O | C=O | NH— | C=O | N | 474 |
| D4 | pyrrolidine-ethoxy | Ph | O | C=O | N= | =CMe— | N | 472 |
| D5 | pyrrolidine-ethoxy | 4-ClPh | bond | C=O | N= | =CH— | N | 476, 478 |

TABLE E

Encompassing compounds of general formula (E), a subset of formula (I) where QY = a thiophene ring fused onto a 6-membered heterocycle composed of groups J, J', J" and J'" and linked via J'"; ML is an oxyethyl group, $R^3$ = Ph; $R^6$ = OMe, Z = a bond

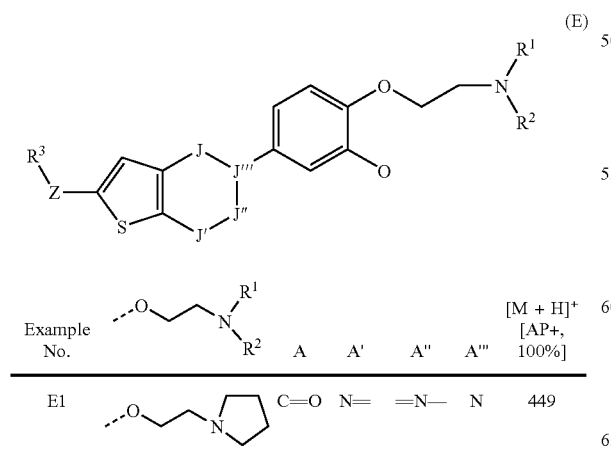

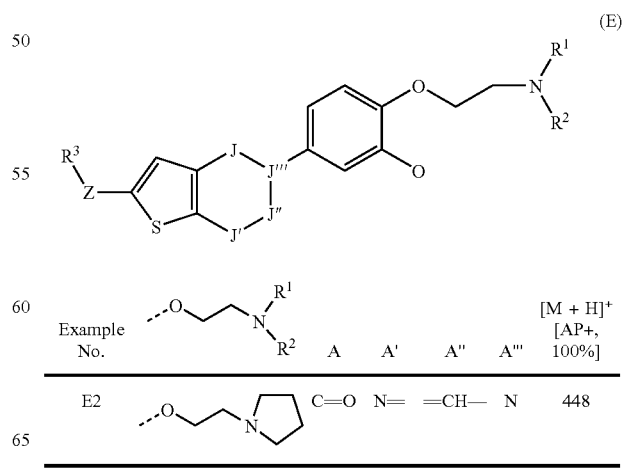

| Example No. | $R^1$ $R^2$ | A | A' | A" | A'" | [M + H]⁺ [AP+, 100%] |
|---|---|---|---|---|---|---|
| E1 | pyrrolidine-ethoxy | C=O | N= | =N— | N | 449 |
| E2 | pyrrolidine-ethoxy | C=O | N= | =CH— | N | 448 |

TABLE F

Encompassing compounds of general formula (F), a subset of formula (I) where QY = a thiophene ring fused onto a 6-membered heterocycle composed of groups J, J', J'' and J''' and linked via J'''; ML is an oxyethyl group, $R^3$ = Ph; $R^6$ = OMe; Z = a bond

| Example No. | -O-CH₂CH₂-N(R¹)(R²) | J | J' | J'' | J''' | [M + H]⁺ [AP+, 100%] |
|---|---|---|---|---|---|---|
| F1 | -O-CH₂CH₂-N-pyrrolidine | C=O | N= | =CH— | N | 448 |
| F2 | -O-CH₂CH₂-N-pyrrolidine | C=O | N= | =C(SMe)— | N | 494 |
| F3 | -O-CH₂CH₂-N-pyrrolidine | C=O | NH | C=S | N | 480 |

TABLE G

Encompassing compounds of general formula (G), a subset of formula (I) where QY = a phthalimide group and Z is O and $R^3$ = Ph (=phenyl).

| Example No. | -N-Ar-(R⁶)ₙ- | ML | R²—N—R¹ | [M + H]⁺ AP+ |
|---|---|---|---|---|
| G1 | 3-OMe phenyl | —(CH₂)₃— | pyrrolidine | 457 |
| G2 | 3-(OCH₂OMe) phenyl | —O—(CH₂)₂— | pyrrolidine | 489 |

TABLE G-continued

Encompassing compounds of general formula (G), a subset of formula (I) where QY = a phthalimide group and Z is O and $R^3$ = Ph (=phenyl).

(G)

[Structure of formula G: phenoxy-phthalimide-N-phenyl(R6)n-ML-N(R1)(R2)]

| Example No. | [N-aryl(R6)n fragment] | ML | $R^2$—N—$R^1$ | $[M + H]^+$ AP+ |
|---|---|---|---|---|
| G3 | [3-(2-methoxyethoxy)-4-yl aniline] | —O—(CH$_2$)$_2$— | pyrrolidin-1-yl | 503 |
| G4 | [3-(methoxymethyl)-4-yl aniline] | —O—(CH$_2$)$_2$— | pyrrolidin-1-yl | 473 |
| G5 | [3-hydroxy-4-yl aniline] | —O—(CH$_2$)$_2$— | pyrrolidin-1-yl | 445 |
| G6 | [3-methoxy-4-yl aniline] | —O—(CH$_2$)$_2$— | pyrrolidin-2-yl | 487 |
| G7 | [3-methoxy-4-yl aniline] | —O—(CH$_2$)$_2$— | pyrrolidin-2-yl | 473 |
| G8 | [3-methoxy-4-yl aniline] | —O—(CH$_2$)$_2$— | piperidin-2-yl | 487 |
| G9 | [3-methoxy-4-yl aniline] | —O—(CH$_2$)$_2$— | 1,2,6-trimethylpiperidinyl | 501 |

TABLE G-continued
Encompassing compounds of general formula (G), a subset of formula (I) where QY = a phthalimide group and Z is O and R³ = Ph (=phenyl).
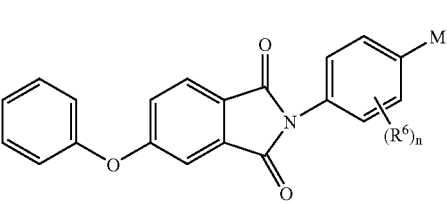
(G)
| Example No. | 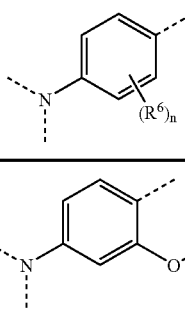 | ML | R²—N—R¹ | [M + H]⁺ AP+ |
|---|---|---|---|---|
| G10 | 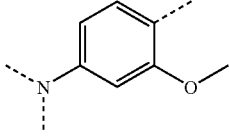 | —O—(CH$_2$)$_2$— | 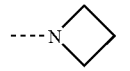 | 529 |
| G11 | 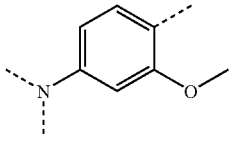 | —O—(CH$_2$)$_2$— | 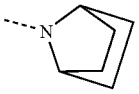 | 445 |
| G12 | 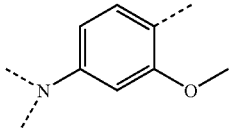 | —O—(CH$_2$)$_2$— | 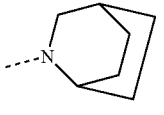 | 485 |
| G13 | 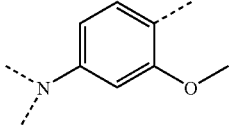 | —O—(CH$_2$)$_2$— | 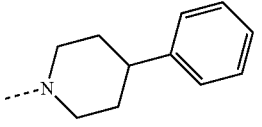 | 499 |
| G14 | 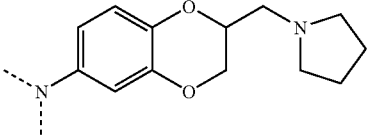 | —O—(CH$_2$)$_2$— | 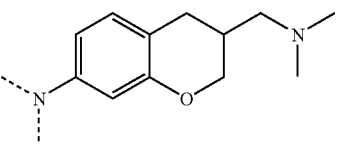 | 549 |
| G15 |  | | | 457 |
| G16 |  | | | 455 |

TABLE G-continued

Encompassing compounds of general formula (G), a subset of formula (I) where QY = a phthalimide group and Z is O and R³ = Ph (=phenyl).

| Example No. | ![aryl with (R⁶)n] | ML | R²—N—R¹ | [M + H]⁺ AP+ |
|---|---|---|---|---|
| G17 | phenyl-N- | tetrahydronaphthalene-CH₂- | pyrrolidine | 453 |
| G18 | phenyl-N- | chromene-CH₂- | pyrrolidine | 453 |
| G19 | phenyl-N- | dihydronaphthalene-CH₂- | pyrrolidine | 451 |
| G20 | methoxyphenyl-N- | —O—(CH₂)₃— | 4-phenylpiperidine | 563 |
| G21 | methoxyphenyl-N- | —O—(CH₂)₃— | pyrrolidine | 473 |
| G22 | methoxyphenyl-N- | —O—(CH₂)₃— | N-methylpiperazine | 502 |
| G23 | methoxyphenyl-N- | —O—(CH₂)₃— | azepane | 501 |

TABLE G-continued

Encompassing compounds of general formula (G), a subset of formula (I) where QY = a phthalimide group and Z is O and $R^3$ = Ph (=phenyl).

(G)

| Example No. | [structure with $(R^6)_n$] | ML | $R^2$—N—$R^1$ | $[M + H]^+$ AP+ |
|---|---|---|---|---|
| G24 | [structure with OMe] | —O—(CH$_2$)$_3$— | [morpholine] | 489 |

Examples given show a pKi in binding to the 353 form of the 11CBy receptor of >6; the most potent examples would have a pKi in the range 7.5–8, for example A5, C5, F1.

The activity of the compounds used in this invention has been assessed by competitive binding assays to 11CBy receptors, as follows:

Radioligand Binding Studies

Radioligand binding assays were carried out on well washed membranes from HEK293 cells stably expressing 11CBy receptors. Membranes (5–15 mg protein) were incubated with [$^{125}$I]-Melanin Concentrating Hormone (0.22 nM) (obtained from NEN) in the presence and absence of competing test compounds for 45 min at 37° C. in a buffer (pH7.4), containing 50 mM Tris and 0.2% BSA. Non-specific binding was defined using 0.1 mM Melanin Concentrating Hormone (obtained from Bachem). The test compounds were added at concentrations between 10M and 10 pM in 10 concentration steps. Following incubation, the reaction was stopped by filtration through GF/B filters and washed with 4×1 ml of ice-cold 50 mM Tris buffer. Microscint 20 (Packard) was added to the filters and the radioactivity measured using a Packard TopCount.

Bound cpm in the presence of test compound was expressed as a fraction of the bound cpm in the absence of test compound and plotted against the concentration of compound. From this an IC50 was determined from which the pKi was calculated.

The compounds described in Examples have a pKi value of greater than 6. For example, the compounds of examples A5, C5 and F1 have a pKi in the range 7.5–8.

Study of Effects of 11CBy Antagonists on Plasma Glucagon and Blood Glucose Levels In chronically femoral artery and vein cannulated conscious CD rats, MCH @ 50 ug/kg (iv) produced 48.7% and 21% increases in plasma glucagon from the pre-treatment value after 5 and 15 minutes respectively. Glucagonotropic effects of MCH produced a maximum rise in blood glucose concentration after 15 min (101%).

Intravenous administration of the title compound from Example A4 (pKi=7.7) at a level of 15 mg/kg five minutes prior to iv bolus injection in the rat glucagon secretion model reduced the rise in plasma glucagon to 2.7% after 15 min with no rise after 5 minutes, while blood glucose increased by only 44%

TABLE 1

Plasma glucagon (pg/ml) and blood glucose levels (mmol/l) in conscious CD rats

| Groups | 0 | 5 min | 15 min |
|---|---|---|---|
| Plasma glucagon | | | |
| Vehicle (1 ml/kg) | 26.3 ± 1.6 (6) | 29.35 ± 3.7 (7) | 25.74 ± 1.3 (7) |
| MCH (50 ug/kg) | 23.6 ± 1.2 (6) | 35.16 ± 2.5 (7) | 28.67 ± 1.61 (7) |
| Example A4 (15 mg/kg) + MCH | 23.45 ± 1.16 (7) | 30.85 ± 2.01 (7) | 22.87 ± 0.56 (5) |
| Blood glucose | | | |
| Vehicle (1 ml/kg) | 6.06 ± 0.11 (7) | 6.14 ± 0.23 (7) | 6.3 ± 0.25 (7) |
| MCH (50 ug/kg) | 5.87 ± 0.22 (7) | 6.5 ± 0.33 (7) | 11.81 ± 1.27 (7) |
| Example A4 (15 mg/kg) + MCH | 5.35 ± 0.23 (7) | 6.46 ± 0.46 (7) | 7.71 ± 0.43 (7) |

Parenthesis = animal numbers. Example A4 given alone produced no change in either plasma glucagon and blood glucose levels. Plasma glucagon determined by commercial RIA kit.

What is claimed is:

1. A compound of formula (I) comprising:

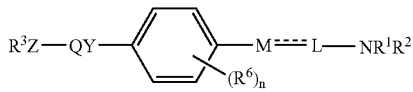

or a salt thereof, wherein
M is a group selected from the group consisting of O, S, C=O, NH and $CH_2$;
L is a 2- or 3-membered alkylene chain;
wherein together M-L may be optionally substituted by at least one moiety selected from the group consisting of methyl, ethyl, hydroxy and $C_{1-3}$ alkoxy;
$R^1$ and $R^2$ together with the nitrogen atom to which they are bonded form a pyrrolidinyl;
each $R^6$ is the same or different and is independently selected from the group consisting of hydroxy, $C_{1-2}$alkyl, $C_{1-3}$alkoxy, halo, $C_{2-3}$alkenyl, benzyl, and —$C(R^a)NOR^b$, wherein $R^a$ and $R^b$ are each independently selected from the group consisting of hydrogen, methyl, methoxymethyl, methoxymethoxy, and methoxyethoxy and n is 1, 2, 3, or 4;
QY is isoindole-1,3-dione; shown below as

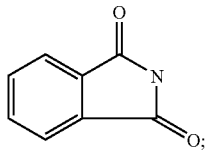

Z is bound to the Q ring and is selected from the group consisting of a direct bond, NH, $NCH_3$, O, S, and $CH_2$; and
$R^3$ is a group selected from the group consisting of aryl, alk-2-en-1-yl, cycloalkyl and cycloalk-2-en-1-yl and wherein said aryl, alk-2-en-1-yl, cycloalkyl, and cycloalk-2-en-1-yl are optionally substituted from 1 to 3 times with a substituent selected from the group consisting of $C_{1-3}$ alkyl, halo, amino, alkylamino, dialkylamino, hydroxy, $C_{1-3}$alkoxy, cyano, trifluoromethyl, and methylthio groups.

2. The compound of claim 1 wherein M is C or $CH_2$.

3. The compound of claim 2 wherein M is O.

4. The compound of claim 1 wherein L is $(CH_2)_2$.

5. The compound of claim 1 wherein L is linked to the phenyl ring of formula (I) via an $R^6$ substituent located in the ortho position relative to the group M to form a bicyclic structure.

6. The compound of claim 5 wherein said bicyclic structure is selected from the group consisting of 1,4-benzodioxan, benzopyran, 1,2-dihydrobenzopyran, 1,2,3,4-tetrahydronaphthalene, and 1,2-dihydronaphthalene.

7. The compound of claim 1 wherein at least one $R^6$ is in the ortho position with respect to the group M.

8. The compound of claim 1 wherein $R^6$ is methoxy.

9. The compound of claim 1 wherein Z is a bond or an oxygen atom.

10. The compound of claim 1 wherein $R^3$ is selected from the group consisting of (i) phenyl which is optionally substituted by halogen, hydroxy, $C_{1-3}$ alkoxy, $C_{1-4}$ alkyl, cyano or trifluoromethyl, (ii) $C_{5-7}$ cycloakyl, (iii) $C_{5-7}$ 2-cycloakenyl, and (iv) $C_{3-6}$ alk-2-en-1-yl.

11. The compound of claim 1 wherein $R^3$ represents phenyl.

12. A pharmaceutical composition comprising a compound of claim 1 or a physiologically acceptable salt thereof and one or more pharmaceutically acceptable carriers or excipients.

13. A method of treating one or more Disorders which comprises administering to a mammal suffering from one or more of the Disorders an effective amount of a compound of claim 1 or a physiologically acceptable salt thereof, wherein said one or more Disorders are selected from the group consisting of obesity, diabetes, depression, schizophrenia, sleep disorder, and anxiety.

14. The method of claim 13 wherein said mammal is a human.

* * * * *